United States Patent
Dubensky, Jr. et al.

(10) Patent No.: US 9,770,467 B2
(45) Date of Patent: Sep. 26, 2017

(54) COMPOSITIONS AND METHODS FOR CANCER IMMUNOTHERAPY

(71) Applicants: THE JOHNS HOPKINS UNIVERSITY, Baltimore, MD (US); ADURO BIOTECH, INC., Berkeley, CA (US)

(72) Inventors: Thomas W. Dubensky, Jr., Piedmont, CA (US); Meredith Lai Ling Leong, Oakland, CA (US); Drew M. Pardoll, Brookeville, MD (US); Young Jun Kim, Ellicott City, MD (US)

(73) Assignees: ADURO BIOTECH, INC., Berkeley, CA (US); THE JOHNS HOPKINS UNIVERSITY, Baltimore, MD (US)

( * ) Notice: Subject to any disclaimer, the term of this patent is extended or adjusted under 35 U.S.C. 154(b) by 145 days.

(21) Appl. No.: 13/912,960

(22) Filed: Jun. 7, 2013

(65) Prior Publication Data

US 2015/0010613 A1 Jan. 8, 2015

Related U.S. Application Data

(60) Provisional application No. 61/657,574, filed on Jun. 8, 2012.

(51) Int. Cl.
| A61K 31/52 | (2006.01) |
| A61K 35/13 | (2015.01) |
| A61K 9/127 | (2006.01) |
| A61K 39/00 | (2006.01) |
| A61K 39/21 | (2006.01) |
| A61K 31/7084 | (2006.01) |
| A61K 38/19 | (2006.01) |
| A61K 38/20 | (2006.01) |
| A61K 39/12 | (2006.01) |

(52) U.S. Cl.
CPC .............. *A61K 35/13* (2013.01); *A61K 9/127* (2013.01); *A61K 31/7084* (2013.01); *A61K 38/19* (2013.01); *A61K 38/193* (2013.01); *A61K 38/195* (2013.01); *A61K 38/208* (2013.01); *A61K 39/0011* (2013.01); *A61K 39/12* (2013.01); *A61K 39/21* (2013.01); *A61K 2039/5152* (2013.01); *A61K 2039/55555* (2013.01); *A61K 2039/55561* (2013.01); *C12N 2740/16034* (2013.01)

(58) Field of Classification Search
None
See application file for complete search history.

(56) References Cited

U.S. PATENT DOCUMENTS

| 5,547,941 A | 8/1996 | Battistini et al. |
| 5,637,483 A | 6/1997 | Dranoff et al. |
| 5,698,432 A | 12/1997 | Oxford |
| 5,904,920 A | 5/1999 | Dranoff et al. |
| 5,985,290 A | 11/1999 | Jaffee et al. |
| 6,033,674 A | 3/2000 | Jaffee et al. |
| 6,090,611 A | 7/2000 | Covacci et al. |
| 6,277,368 B1 | 8/2001 | Hiserodt et al. |
| 6,350,445 B1 | 2/2002 | Jaffee et al. |
| 6,464,973 B1 | 10/2002 | Levitsky et al. |
| 6,558,670 B1 | 5/2003 | Friede et al. |
| 6,780,429 B1 | 8/2004 | Matsuyama et al. |
| 7,569,555 B2 | 8/2009 | Karaolis |
| 7,592,326 B2 | 9/2009 | Karaolis |
| 7,709,458 B2 | 5/2010 | Karaolis et al. |
| 8,012,469 B2 | 9/2011 | Levitsky et al. |
| 8,283,328 B2 | 10/2012 | Krieg et al. |
| 8,304,396 B2 | 11/2012 | Krieg et al. |
| 8,367,716 B2 | 2/2013 | Karaolis |
| 8,450,293 B2 | 5/2013 | Jones et al. |
| 9,061,048 B2 | 6/2015 | Portnoy et al. |
| 2001/0041682 A1 | 11/2001 | Stutts et al. |
| 2002/0140414 A1 | 10/2002 | Sohn et al. |
| 2002/0150588 A1 | 10/2002 | Allison et al. |
| 2003/0003092 A1 | 1/2003 | Krissansen et al. |
| 2003/0138413 A1* | 7/2003 | Vicari et al. ............... 424/93.21 |
| 2005/0281783 A1 | 12/2005 | Kinch et al. |
| 2006/0040887 A1 | 2/2006 | Karaolis |
| 2006/0286549 A1 | 12/2006 | Sohn et al. |

(Continued)

FOREIGN PATENT DOCUMENTS

| WO | WO 03070234 A1 * | 8/2003 | ............. A61K 31/13 |
| WO | 2005030186 A2 | 4/2005 | |

(Continued)

OTHER PUBLICATIONS

Jin et al. ("Jin", J. Immunol., 2011, 187, 2595-2601).*
Gao et al. ("Gao", Vaccine, 2006, 24, 5265-5268).*
Dalby et al. ("Dalby", Methods, 2004, 33, 95-103).*
Berenbaum (Clin. Exp Immunol. 28:1-18, 1977.*
http://weisenthal.org/feedback.html, Feb. 4, 2002.*
Chou, T-C (Cancer Res. Jan. 15, 2010 70(2): 440-446).*
Topalian et al., Cancer Immunotherapy Comes of Age. J Clin Oncol. Dec. 20, 2011;29(36):4828-4836.

(Continued)

*Primary Examiner* — Peter J Reddig
*Assistant Examiner* — Kauser Akhoon
(74) *Attorney, Agent, or Firm* — Acuity Law Group, PC; Michael A. Whittaker

(57) ABSTRACT

The present invention provides a combination therapy which relies on a small molecule immune stimulator—cyclic-dinucleotide (CDN)—that activates DCs via a recently discovered cytoplasmic receptor known as STING (Stimulator of Interferon Genes) formulated with allogeneic human tumor cell lines engineered to secrete high amounts of GM-CSF. This combination therapy can provide an ideal synergy of multiple tumor associated antigens, DC recruitment and proliferation, coupled with a potent DC activation stimulus.

9 Claims, 10 Drawing Sheets

(56) References Cited

U.S. PATENT DOCUMENTS

| | | |
|---|---|---|
| 2007/0059683 A1 | 3/2007 | Barber et al. |
| 2007/0224210 A1 | 9/2007 | Krieg et al. |
| 2007/0244059 A1 | 10/2007 | Karaolis |
| 2007/0281897 A1 | 12/2007 | Karaolis |
| 2008/0076778 A1 | 3/2008 | Ossovskaya et al. |
| 2008/0286296 A1 | 11/2008 | Ebensen et al. |
| 2010/0150946 A1 | 6/2010 | Jooss et al. |
| 2010/0310602 A1 | 12/2010 | Reed et al. |
| 2011/0081674 A1 | 4/2011 | Han et al. |
| 2011/0262485 A1 | 10/2011 | Barber |
| 2011/0287948 A1 | 11/2011 | Suresh et al. |
| 2012/0041057 A1 | 2/2012 | Jones et al. |
| 2012/0164107 A1 | 6/2012 | Portnoy et al. |
| 2012/0178710 A1 | 7/2012 | Jones et al. |
| 2014/0155345 A1 | 6/2014 | Jones et al. |
| 2014/0329889 A1 | 11/2014 | Vance et al. |
| 2014/0341976 A1 | 11/2014 | Dubensky et al. |
| 2015/0056224 A1 | 2/2015 | Dubensky et al. |
| 2016/0068560 A1 | 3/2016 | Patel et al. |
| 2016/0210400 A1 | 7/2016 | Patel et al. |

FOREIGN PATENT DOCUMENTS

| | | |
|---|---|---|
| WO | 2005039535 A1 | 5/2005 |
| WO | 2005087238 A2 | 9/2005 |
| WO | 2005089777 A1 | 9/2005 |
| WO | 2007054279 A2 | 5/2007 |
| WO | 2007064945 A2 | 6/2007 |
| WO | 2009133560 A1 | 11/2009 |
| WO | 2010017248 A2 | 2/2010 |
| WO | 2010067262 A1 | 6/2010 |
| WO | 2010104833 A1 | 9/2010 |
| WO | 2010104883 A1 | 9/2010 |
| WO | 2011003025 A1 | 1/2011 |
| WO | 2011136828 A1 | 11/2011 |
| WO | 2011139769 A2 | 11/2011 |
| WO | 2012068360 A1 | 5/2012 |
| WO | 2012088155 A1 | 6/2012 |
| WO | 2012139209 A1 | 10/2012 |
| WO | 2013086331 A1 | 6/2013 |
| WO | 2013166000 A1 | 11/2013 |
| WO | 2013185052 A1 | 12/2013 |
| WO | 2014093936 A1 | 6/2014 |
| WO | 2014099824 A1 | 6/2014 |
| WO | 2014179335 A1 | 11/2014 |
| WO | 2014179760 A1 | 11/2014 |
| WO | 2014189805 A1 | 11/2014 |
| WO | 2014189806 A1 | 11/2014 |

OTHER PUBLICATIONS

Van Elsas et al., Elucidating the Autoimmune and Antitumor Effector Mechnaisms of a Treatment Based on Cytotoxic T Lymphocyte Antigen-4 Blockade in Combination with a B16 Melanoma Vaccine: Comparison of Prophylaxis and Therapy. J Exp Med. Aug. 20, 2001;194(4):481-489.

Van Erp et al., Application of a Sol Particle Immunoassay to the Determination of Affinity Constants of Monoclonal Antibodies. J Immunoassay. 1991;12(3):425-443.

Waitz et al., Potent Induction of Tumor Immunity by Combining Tumor Cryoablation with Anti-CTLA-4 Therapy. Cancer Res. Jan. 15, 2012;72(2):430-439.

Ward et al., Binding activities of a repertoire of single immunoglobulin variable domains secreted from *Escherichia coli*. Nature. Oct. 12, 1989;341(6242):544-546.

Wilson et al., Simplified conjugation chemistry for coupling peptides to F(ab') fragments: autologous red cell agglutination assay for HIV-1 antibodies. J Immunol Methods. Oct. 14, 1994;175(2):267-273.

Witte et al., Innate Immune Pathways Triggered by Listeria monocytogenes and Their Role in the Induction of Cell-Mediated Immunity. Adv Immunol. 2012;113:135-156.

Woodward et al., c-di-AMP Secreted by Intracellular Listeria monocytogenes Activates a Host Type I Interferon Response. Science. Jun. 25, 2010;328(5986):1703-1705.

Yan et al., Synthesis and immunostimulatory properties of the phosphorothioate analogues of cdiGMP. Bioorg Med Chem Lett. Oct. 15, 2008;18(20):5631-5634.

Yarmush et al., Coupling of antibody-binding fragments to solid-phase supports: site-directed binding of F(ab')2 fragments. J Biochem Biophys Methods. Dec. 1992;25(4):285-297.

Adler-Moore et al., Characterization of the murine Th2 response to immunization with liposomal M2e influenza vaccine. Vaccine. Jun. 15, 2011;29(27):4460-8.

Ahmed et al., Assessing the Safety of Adjuvanted Vaccines. Sci Transl Med. Jul. 27, 2011;3(93):93rv2.

Antonarakis and Drake, Combining immunological and androgen-directed approaches: an emerging concept in prostrate cancer immunotherapy. Curr Opin Oncol. May 2012;24(3):258-265.

Bahjat et al., Cytosolic Entry Controls CD8+-T-Cell Potency during Bacterial Infection. Infect Immun. Nov. 2006;74(11):6387-97.

Bahjat et al., Activation of Immature Hepatic NK Cells as Immunotherapy for Liver Metastatic Disease. J Immunol. Dec. 1, 2007;179(11):7376-84.

Barber , STING-dependent signaling. Nat Immunol. Sep. 20, 2011;12(10):929-930.

Blankenstein et al., The determinants of tumour immunogenicity. Nat Rev Cancer. Mar. 1, 2012:12(4):307-313.

Brahmer et al., Phase I Study of Single-Agent Anti-Programmed Death-1 (MDX-1106) in Refractory Solid Tumors: Safety, Clinical Activity, Pharmacodynamics, and Immunologic Correlates. J Clin Oncol. Jul. 1, 2010;28(19):3167-3175.

Brockstedt et al., Listeria-based cancer vaccines that segregate immunogenicity from toxicity. Proc Natl Acad Sci U S A. Sep. 21, 2004;101(38):13832-13837.

Burdette et al., STING is a direct innate immune sensor of cyclic-di-GMP. Nature. Sep. 25, 2011;478(7370):515-518.

Coffman et al., Vaccine Adjuvants: Putting Innate Immunity to Work. Immunity. Oct. 29, 2010;33(4):492-503.

International Search Report and Written Opinion issued in PCT/US20131044744 dated Nov. 7, 2013.

Crimmins et al., Listeria monocytogenes multidrug resistance transporters activate a cytosolic surveillance pathway of innate immunity. Proc Natl Acad Sci USA. Jul. 22, 2008;105(29):10191-10196.

Crittenden et al., Expression of Inflammatory Chemokines Combined with Local Tumor Destruction Enhances Tumor Regression and Long-term Immunity. Cancer Res. Sep. 1, 2003;63(17):5505-5512.

Curran et al., Tumor Vaccines Expressing Flt3 Ligand Synergize with CTLA-4 Blockade to Reject Preimplanted Tumors. Cancer Res. Oct. 1, 2009;69(19):7747-7755.

Di Lorenzo et al., Immunotherapy for the treatment of prostate cancer. Nat Rev Clin Oncol. May 24, 2011;8(9):551-561.

Drake et al., Androgen ablation mitigates tolerance to a prostate/prostate cancer-restricted antigen. Cancer Cell. Mar. 2005;7(3):239-249.

Dranoff et al., Vaccination with irradiated tumor cells engineered to secrete murine granulocyte-macrophage colony-stimulating factor stimulates potent, specific, and long-lasting anti-tumor immunity. Proc Natl Acad Sci USA. Apr. 15, 1993;90(8):3539-3543.

Driessens et al., Highly Successful Therapeutic Vaccinations Combining Factor Dendritic Cells and Tumor Cells Secreting Granulocyte Macrophage Colony-stimulating Factor. Cancer Res. Nov. 15, 2004;64(22):8435-8442.

Dubensky and Reed, Adjuvants for cancer vaccines. Semin Immunol. Jun. 2010;22(3):155-161.

Dubensky et al., Rationale, progress, and development of vaccines utilizing STING-activating cyclic dinucleotide adjuvants. Ther Adv Vaccines. Nov. 2013;1(4):131-143.

Eager and Nemunaitis, GM-CSF Gene-Transduced Tumor Vaccines. Mol Ther. Jul. 2005;12(1):18-27.

Einstein et al., Comparison of the immunogenicity and safety of Cervarix and Gardasil human papillomavirus (HPV) cervical cancer vaccines in healthy women aged 18-45 years. Hum Vaccin. Oct. 2009;5(10):705-719.

(56) References Cited

OTHER PUBLICATIONS

Fasso et al., SPAS-1 (stimulator of prostatic adenocarcinomaspecific T cells)/SH3GLB2: A prostate tumor antigen identified by CTLA-4 blockade. Proc Natl Acad Sci U S A. Mar. 4, 2008;105(9):3509-3514.
Goldberg et al., Role of PD-1 and its ligand, B7-H1, in early fate decisions of CD8 T cells. Blood. Jul. 1, 2007;110(1):186-192.
Gulley et al., Immunologic and Prognostic Factors Associated with Overall Survival Employing a Poxviral-based PSA Vaccine in Metastatic Castrate-resistant Prostate Cancer. Cancer Immunol Immunother. May 2010;59(5):663-674.
Hernandez et al., Novel Kidney Cancer Immunotherapy Based on the Granulocyte-Macrophage Colony-stimulating Factor and Carbonic Anhydrase IX Fusion Gene. Clin Cancer Res. May 2003;9(5):1906-1916.
Hodi et al., Improved Survival with Ipilimumab in Patients with Metastatic Melanoma. N Engl J Med. Aug. 19, 2010;363(8):711-23.
Hurwitz et al., The TRAMP Mouse as a Model for Prostate Cancer. Curr Protoc Immunol. Nov. 2001;Chapter 20:Unit 20.5.
Ishikawa and Barber, The STING pathway and regulation of innate immune signaling in response to DNA pathogens. Cell Mol Life Sci. Apr. 2011;68(7):1157-1165.
Jemal et al., Cancer Statistics, 2010. CA Cancer J Clin. Sep.-Oct. 2010;60(5):277-300.
Kantoff et al., Overall Survival Analysis of a Phase II Randomized Controlled Trial of a Poxviral-Based PSA-Targeted Immunotherapy in Metastatic Castration-Resistant Prostate Cancer. J Clin Oncol. Mar. 1, 2010;28(7):1099-1105.
Kantoff et al., Sipuleucel-T Immunotherapy for Castration-Resistant Prostate Cancer. N Engl J Med. Jul. 29, 2010;363(5):411-422.
Kastenmuller et al., Protective T cell immunity in mice following protein-TLR7/8 agonist-conjugate immunization requires aggregation, type I IFN, and multiple DC subsets. J Clin Invest. May 2011;121(5):1782-1796.
Kasturi et al., Programming the magnitude and persistence of antibody responses with innate immunity. Nature. Feb. 24, 2011;470(7335):543-7.
Le et al., A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction. Clin Cancer Res. Feb. 1, 2012;18(3):858-868.
Le et al., Cellular Vaccine Approaches. Cancer J. Jul.-Aug. 2010;16(4):304-10.
Leber et al., Distinct TLR- and NLR-Mediated Transcriptional Responses to an Intracellular Pathogen. PLoS Pathog. Jan. 2008;4(1):e6.
Lutz et al., A Lethally Irradiated Allogeneic Granulocyte-Macrophage Colony Stimulating Factor-Secreting Tumor Vaccine for Pancreatic Adenocarcinoma: A Phase II Trial of Safety, Efficacy, and Immune Activation. Ann Surg. Feb. 2011;253(2):328-335.
Mellman et al., Cancer immunotherapy comes of age. Nature. Dec. 21, 2011;480(7378):480-489.
Muderhwa et al., Oil-in-Water Liposomal Emulsions: Characterization and Potential Use in Vaccine Delivery. J Pharm Sci. Dec. 1999;88(12):1332-1339.
Nelson and Griswold, A computer program for calculating antibody affinity constants. Comput Methods Programs Biomed. Jul.-Aug. 1988;27(1):65-68.
Olson et al., Liposomal gD Ectodomain (gD1-306) Vaccine Protects Against HSV2 Genital or Rectal Infection of Female and Male Mice. Vaccine. Dec. 11, 2009;28(2):548-560.
O'Riordan et al., Innate recognition of bacteria by a macrophage cytosolic surveillance pathway. Proc Natl Acad Sci USA. Oct. 15, 2002;99(21):13861-13866.
Pardoll and Drake, Immunotherapy earns its spot in the ranks of cancer therapy. J Exp Med. Feb. 13, 2012;209(2):201-209.
Pardoll, The blockade of immune checkpoints in cancer immunotherapy. Nat Rev Cancer. Mar. 22, 2012;12(4):252-264.
Reed et al., New horizons in adjuvants for vaccine development. Trends Immunol. Jan. 2009;30(1):23-32.
Sun and Bevan, Defective CD8 T Cell Memory Following Acute Infection Without CD4 T Cell Help. Science. Apr. 11, 2003;300(5617):339-342.
Tannock et al., Docetaxel plus Prednisone or Mitoxantrone plus Prednisone for Advanced Prostate Cancer. N Engl J Med. Oct. 7, 2004;351(15):1502-1512.
Matsushita et al., Preferentially Expressed Antigen of Melanoma (PRAME) in the Development of Diagnostic and Therapeutic Methods for Hematological Malignancies. Leuk Lymphoma. Mar. 2003;44(3):439-444.
Mayo et al., Mdm-2 Phosphorylation by DNA-dependent Protein Kinase Prevents Interaction with p53. Cancer Res. Nov. 15, 1997;57(22):5013-5016.
McCool et al., Roles of calreticulin and calnexin during mucin synthesis in LS180 and HT29/A1 human colonic adenocarcinoma cells. Biochem J. Aug. 1, 1999;341 ( Pt 3):593-600.
McCune et al., Active specific immunotherapy with tumor cells and Corynebacterium parvum: A phase I study. Cancer. May 1979;43(5):1619-1623.
McWhirter et al., A host type I interferon response is induced by cytosolic sensing of the bacterial second messenger cyclic-di-GMP. J Exp Med. Aug. 31, 2009;206(9):1899-1911.
Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.
Molijn et al., Molecular diagnosis of human papillomavirus (HPV) infections. J Clin Virol. Mar. 2005;32 Suppl 1: S43-51.
Moreau-Aubry et al., A Processed Pseudogene Codes for a New Antigen Recognized by a Cd8+ T Cell Clone on Melanoma. J Exp Med. May 1, 2000;191(9):1617-1624.
Morse et al., A Phase I Study of Active Immunotherapy with Carcinoembryonic Antigen Peptide (CAP-1)-pulsed, Autologous Human Cultured Dendritic Cells in Patients with Metastatic Malignancies Expressing Carcinoembryonic Antigen. Clin Cancer Res. Jun. 1999;5(6):1331-1338.
Mukhopadhyay et al., A structural perspective of the flavivirus life cycle. Nat Rev Microbiol. Jan. 2005;3(1):13-22.
Mulders et al., Tumor antigens and markers in renal cell carcinoma. Urol Clin North Am. Aug. 2003;30(3):455-465.
Muller et al., MeCP2 and MBD2 expression in human neoplastic and non-neoplastic breast tissue and its association with oestrogen receptor status. Br J Cancer. Nov. 17, 2003;89(10):1934-1939.
Muminova et al., Characterization of human mesothelin transcripts in ovarian and pancreatic cancer. BMC Cancer. May 12, 2004;4:19.
Nair et al., Induction of cytotoxic T cell responses and tumor immunity against unrelated tumors using telomerase reverse transcriptase RNA transfected dendritic cells. Nat Med. Sep. 2000;6(9):1011-1017.
Nakatsura et al., Glypican-3, overexpressed specifically in human hepatocellular carcinoma, is a novel tumor marker. Biochem Biophys Res Commun. Jun. 20, 2003;306(1):16-25.
Nakatsura et al., Identification of Glypican-3 as a Novel Tumor Marker for Melanoma. Clin Cancer Res. Oct. 1, 2004;10(19):6612-6621.
Neumann et al., Identification of an HLA-DR-restricted peptide epitope with a promiscuous binding pattern derived from the cancer testis antigen HOM-MEL-40/SSX2. Int J Cancer. Nov. 20, 2004;112(4):661-668.
Nicoletto et al., BRCA-1 and BRCA-2 mutations as prognostic factors in clinical practice and genetic counselling. Cancer Treat Rev. Oct. 2001;27(5):295-304.
Oberste et al., Evidence for Frequent Recombination within Species Human Enterovirus B Based on Complete Genomic Sequences of All Thirty-Seven Serotypes. J Virol. Jan. 2004;78(2):855-867.
Oberthuer et al., The Tumor-Associated Antigen PRAME Is Universally Expressed in High-Stage Neuroblastoma and Associated with Poor Outcome. Clin Cancer Res. Jul. 1, 2004;10(13):4307-4313.
Ogunniyi et al., c-di-GMP is an Effective Immunomodulator and Vaccine Adjuvant Against Pneumococcal Infection. Vaccine. Aug. 26, 2008;26(36):4676-4685.

(56) References Cited

OTHER PUBLICATIONS

Oliveira-Ferreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.
Orvell et al., Antigenic relationships between six genotypes of the small hydrophobic protein gene of mumps virus. J Gen Virol. Oct. 2002;83(Pt 10):2489-2496.
Otte et al., MAGE-A Gene Expression Pattern in Primary Breast Cancer. Cancer Res. Sep. 15, 2001;61(18):6682-6687.
Ouyang et al., Structural Analysis of the STING Adaptor Protein Reveals a Hydrophobic Dimer Interface and Mode of Cyclic di-GMP Binding. Immunity. Jun. 29, 2012;36(6):1073-1086.
Oyston and Quarry, Tularemia vaccine: past, present and future. Antonie Van Leeuwenhoek. May 2005;87(4):277-281.
Padilla et al., Imaging of the varicella zoster virion in the viral highways: Comparison with herpes simplex viruses 1 and 2, cytomegalovirus, pseudorabies virus, and human herpes viruses 6 and 7. J Med Virol. 2003;70 Suppl 1:S103-S110.
Patel et al., Development of a simple restriction fragment length polymorphism assay for subtyping of coxsackie B viruses. J Virol Methods. Sep. 15, 2004;120(2):167-172.
Peh et al., Frequent presence of subtype A virus in Epstein-Barr virus-associated malignancies. Pathology. Oct. 2002; 34(5):446-450.
Pham et al., Exploiting cross-priming to generate protective CD8 T-cell immunity rapidly. Proc Natl Acad Sci U S A. Jul. 6, 2010;107(27):12198-12203.
Pisarev et al., Full-length dominant-negative survivin for cancer immunotherapy. Clin Cancer Res. Dec. 15, 2003;9(17):6523-6533.
Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. Nov. 2004;11(6):1008-1015.
Rappuoli et al., Vaccines for the twenty-first century society. Nat Rev Immunol. Nov. 4, 2011;11(12):865-872.
Renkvist et al., A listing of human tumor antigens recognized by T cells. Cancer Immunol Immunother. Mar. 2001;50(1):3-15.
Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.
Rezig et al., Molecular Characterization of Coxsackievirus B5 Isolates. J Med Virol. Feb. 2004;72(2):268-274.
Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26(3):817-824.
Roden and Wu, Preventative and therapeutic vaccines for cervical cancer. Expert Rev Vaccines. Aug. 2003;2(4):495-516.
Roner et al., Identification of signals required for the insertion of heterologous genome segments into the reovirus genome. Proc Natl Acad Sci U S A. Dec. 19, 1995;92(26):12362-12366.
Ross et al., The Cyclic Diguanylic Acid Regulatory System of Cellulose Synthesis in Acetobacter xylinum. Chemical synthesis and biological activity of cyclic nucleotide dimer, trimer, and phosphothioate derivatives. J Biol Chem. Nov. 5, 1990;265(31):18933-18943.
Salazar-Onfray et al., Synthetic peptides derived from the melanocyte-stimulating hormone receptor MC1R can stimulate HLA-A2-restricted cytotoxic T lymphocytes that recognize naturally processed peptides on human melanoma cells. Cancer Res. Oct. 1, 1997;57(19):4348-4355.
Santin et al., The serine protease stratum corneum chymotryptic enzyme (kallikrein 7) is highly overexpressed in squamous cervical cancer cells. Gynecol Oncol. Aug. 2004;94(2):283-288.
Sarcevic et al., Expression of Cancer/Testis Tumor Associated Antigens in Cervical Squamous Cell Carcinoma. Oncology. 2003;64(4):443-449.
Sarobe et al., Carcinoembryonic Antigen as a Target to Induce Anti-Tumor Immune Responses. Curr Cancer Drug Targets. Aug. 2004;4(5):443-454.
Sasaki et al., SAGE mRNA expression in advanced-stage lung cancers. Eur J Surg Oncol. Dec. 2003;29(10):900-903.
Sasatomi et al., Expression of tumor rejection antigens in colorectal carcinomas. Cancer. Mar. 15, 2002;94(6):1636-1641.
Sauer et al., The N-Ethyl-N-Nitrosourea-Induced Goldenticket Mouse Mutant Reveals an Essential Function of Sting in the In Vivo Interferon Response to Listeria monocytogenes and Cyclic Dinucleotides. Infect Immun. Feb. 2011;79(2):688-694.
Scanlan et al., Antigens recognized by autologous antibody in patients with renal-cell carcinoma. Int J Cancer. Nov. 12, 1999;83(4):456-464.
Scanlan et al., Cancer-related serological recognition of human colon cancer: identification of potential diagnostic and immunotherapeutic targets. Cancer Res. Jul. 15, 2002;62(14):4041-4047.
Scanlan et al., Expression of cancer-testis antigens in lung cancer: definition of bromodomain testis-specific gene (BRDT) as a new CT gene, CT9. Cancer Lett. Mar. 31, 2000;150(2):155-164.
Scanlan et al., Humoral immunity to human breast cancer: antigen definition and quantitative analysis of mRNA expression. Cancer Immun. Mar. 30, 2001;1:4.
Scanlan et al., The cancer/testis genes: review, standardization, and commentary. Cancer Immun. Jan. 23, 2004;4:1.
Scarcella et al., Expression of MAGE and GAGE in high-grade brain tumors: a potential target for specific immunotherapy and diagnostic markers. Clin Cancer Res. Feb. 1999;5(2):335-341.
Schmidt et al., Memory CD8 T cell responses exceeding a large but definable threshold provide long-term immunity to malaria. Proc Natl Acad Sci U S A. Sep. 16, 2008;105(37):14017-14022.
Schmittgen et al., Expression of prostate specific membrane antigen and three alternatively spliced variants of PSMA in prostate cancer patients. Int J Cancer. Nov. 1, 2003;107(2):323-329.
Schwartz et al., Hyperinduction of Host Beta Interferon by a Listeria monocytogenes Strain Naturally Overexpressing the Multidrug Efflux Pump MdrT. Infect Immun. Apr. 2012;80(4):1537-1545.
Schwartz et al., Novel targeted and immunotherapeutic strategies in chronic myeloid leukemia. Semin Hematol. Jan. 2003;40(1):87-96.
Seder et al., T-cell quality in memory and protection: implications for vaccine design. Nat Rev Immunol. Apr. 2008;8(4):247-258.
Sepehr et al., Distinct pattern of TP53 mutations in squamous cell carcinoma of the esophagus in Iran. Oncogene. Nov. 1, 2001;20(50):7368-7374.
Shanahan et al., Differential analog binding by two classes of c-di-GMP riboswitches. J Am Chem Soc. Oct. 5, 2011;133(39):15578-15592.
Shigemasa et al., Expression of the protease inhibitor antileukoprotease and the serine protease stratum corneum chymotryptic enzyme (SCCE) is coordinated in ovarian tumors. Int J Gynecol Cancer. Nov.-Dec. 2001;11(6):454-461.
Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.
Shirasawa et al., Receptor for advanced glycation end-products is a marker of type I lung alveolar cells. Genes Cells. Feb. 2004;9(2):165-174.
Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64(11):3757-3760.
Shu et al., Structure of STING bound to c-di-GMP Reveals the Mechanism of Cyclic Dinucleotide Recognition by the Immune System. Nat Struct Mol Biol. Jun. 24, 2012;19(7):722-724.
Siegel et al., Induction of antitumour immunity using survivin peptide-pulsed dendritic cells in a murine lymphoma model. Br J Haematol. Sep. 2003;122(6):911-914.
Simon et al., Cervical response to vaccination against HPV16 E7 in case of severe dysplasia. Eur J Obstet Gynecol Reprod Biol. Aug. 15, 2003;109(2):219-223.

(56) References Cited

OTHER PUBLICATIONS

Singh et al., Avian influenza viral nucleocapsid and hemagglutinin proteins induce chicken CD8+ memory T lymphocytes. Virology 2010;399:231-238.

Singh et al., Non-replicating adenovirus vectors expressing avian influenza virus hemagglutinin and nucleocapsid proteins induce chicken specific effector, memory and effector memory CD8(+) T lymphocytes. Virology. Sep. 15, 2010;405(1):62-69.

Sjolander et al., Serological divergence of Dobrava and Saaremaa hantaviruses: evidence for two distinct serotypes. Epidemiol Infect. Feb. 2002;128(1):99-103.

Skoberne et al., KBMA Listeria monocytogenes is an effective vector for DC-mediated induction of antitumor immunity. J Clin Invest. Dec. 2008;118(12):3990-4001.

Slager et al., Identification of multiple HLA-DR-restricted epitopes of the tumor-associated antigen CAMEL by CD4+ Th1/Th2 lymphocytes. J Immunol. Apr. 15, 2004;172(8):5095-5102.

Slager et al., Induction of CAMEL/NY-ESO-ORF2-specific CD8+ T cells upon stimulation with dendritic cells infected with a modified Ad5 vector expressing a chimeric Ad5/35 fiber. Cancer Gene Ther. Mar. 2004;11(3):227-236.

Small et al., Immunotherapy of Hormone-Refractory Prostate Cancer With Antigen-Loaded Dendritic Cells. J Clin Oncol. Dec. 1, 2000;18(23):3894-3903.

Smith et al., Neutralization of HIV-1 Subtypes: Implications for Vaccine Formulations. J Med Virol. Nov. 1998;56(3):264-268.

Smits et al., Phylogenetic and Evolutionary Relationships among Torovirus Field Variants: Evidence for Multiple Intertypic Recombination Events. J Virol. Sep. 2003;77(17):9567-9577.

Sofia et al., Nucleoside, Nucleotide, and Non-Nucleoside Inhibitors of Hepatitis C Virus NS5B RNA—Dependent RNA—Polymerase. J Med Chem. Mar. 22, 2012;55(6):2481-2531.

Sofia, Nucleotide Prodrugs for HCV Therapy. Antivir Chem Chemother. Aug. 23, 2011;22(1):23-49.

Stams et al., Expression Levels ofTEL, AML1, and the Fusion ProductsTEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8):2974-2980.

Steffens et al., Immunohistochemical analysis of tumor antigen saturation following injection of monoclonal antibody G250. Anticancer Res. Mar.-Apr. 1999;19(2A):1197-1200.

Stirnadel et al., Assessment of different sources of variation in the antibody responses to specific malaria antigens in children in Papua New Guinea. Int J Epidemiol. Jun. 2000;29(3):579-586.

Stolier et al., Initial experience with surgical treatment planning in the newly diagnosed breast cancer patient at high risk for BRCA-1 or BRCA-2 mutation. Breast J. Nov.-Dec. 2004;10(6):475-480.

Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.

Sun et al., Cyclic GMP-AMP Synthase Is a Cytosolic DNA Sensor That Activates the Type I Interferon Pathway. Science. Feb. 15, 2013;339(6121):786-791.

Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.

Suzuki et al., Practical Synthesis of Cyclic Bis(3'-5')diadenylic Acid (c-di-AMP). Chem Lett. 2011;40(10):1113-1114.

Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8):1363-1370.

Tamayo et al., Roles of Cyclic Diguanylate in the Regulation of Bacterial Pathogenesis. Annu Rev Microbiol. 2007;61:131-148.

Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.

Tanaka and Chen, STING Specifies IRF3 Phosphorylation by TBK1 in the Cytosolic DNA Signaling Pathway. Sci Signal. Mar. 6, 2012;5(214):ra20.

Tanaka et al., Expression of Tumor-Rejection Antigens in Gynecologic Cancers. Jpn J Cancer Res. Nov. 2000;91(11):1177-1184.

Tannapfel et al., BRAF Gene Mutations Are Rare Events in Gastroenteropancreatic Neuroendocrine Tumors. Am J Clin Pathol. Feb. 2005;123(2):256-260I.

Tewari et al., Poly(I:C) is an effective adjuvant for antibody and multi-functional CD4+ T cell responses to Plasmodium falciparum circumsporozoite protein (CSP) and αDEC-CSP in Non Human Primates. Vaccine. Oct. 21, 2010;28(45):7256-7266.

Treurnicht et al., HHV-8 subtypes in South Africa: identification of a case suggesting a novel B variant. J Med Virol. Feb. 2002;66(2):235-240.

Trimble et al., Comparison of the CD8+ T cell responses and antitumor effects generated by DNA vaccine administered through gene gun, biojector, and syringe. Vaccine. Sep. 8, 2003;21(25-26):4036-4042.

Trincado et al., Human Cytomegalovirus Strains Associated With Congenital and Perinatal Infections. J Med Virol. Aug. 2000;61(4):481-487.

Tsang et al., Phenotypic Stability of a Cytotoxic T-Cell Line Directed Against an Immunodominant Epitope of Human Carcinoembryonic Antigen. Clin Cancer Res. Dec. 1997;3(12 Pt 1):2439-2449.

Tsao and Sober, Melanoma Treatment Update. Dermatol Clin. Apr. 2005;23(2):323-333.

Tsuruma et al., Phase I clinical study of anti-apoptosis protein, survivin-derived peptide vaccine therapy for patients with advanced or recurrent colorectal cancer. J Transl Med. Jun. 13, 2004;2(1):19 (11 pages).

Vallejo et al., Nucleotide Sequence and Restriction Fragment-Length Polymorphism Analysis of Human T-Cell Lymphotropic Virus Type II (HTLV-II) in Southern Europe: Evidence for the HTLV-IIa and HTLV-IIb Subtypes. J Acquir Immune Defic Syndr Hum Retrovirol. Dec. 1, 1996;13(4):384-391.

Van Den Eynde et al., A New Antigen Recognized by Cytolytic T Lymphocytes on a Human Kidney Tumor Results From Reverse Strand Transcription. J Exp Med. Dec. 20, 1999;190(12):1793-1800.

Vance et al., Patterns of Pathogenesis: Discrimination of Pathogenic and Nonpathogenic Microbes by the Innate Immune System. Cell Host Microbe. Jul. 23, 2009;6(1):10-21.

Vandamme et al., African Origin of Human T-Lymphotropic Virus Type 2 (HTLV-2) Supported by a Potential New HTLV-2d Subtype in Congolese Bambuti Efe Pygmies. J Virol. May 1998;72(5):4327-4340.

Vilas Boas et al., Cytomegalovirus Glycoprotein B Genotypes and Central Nervous System Disease in AIDS Patients. J Med Virol. Nov. 2003;71(3):404-407.

Vilchez and Butel, Emergent Human Pathogen Simian Virus 40 and Its Role in Cancer. Clin Microbiol Rev. Jul. 2004;17(3):495-508.

Virok et al., Chlamydial Infection Induces Pathobiotype-Specific Protein Tyrosine Phosphorylation in Epithelial Cells. Infect Immun. Apr. 2005;73(4):1939-1946.

Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4)1687-1697.

Waltregny et al., Screening of histone deacetylases (HDAC) expression in human prostate cancer reveals distinct class I HDAC profiles between epithelial and stromal cells. Eur J Histochem. Jul.-Sep. 2004;48(3):273-290.

Wang et al., Alterations of APC, c-met, and p53 Genes in Tumor Tissue and Serum of Patients with Gastric Cancers. J Surg Res. Aug. 2004;120(2):242-248.

Wang et al., Cloning Genes Encoding MHC Class II—Restricted Antigens: Mutated CDC27 as a Tumor Antigen. Science. May 21, 1999;284(5418):1351-1354.

Wang et al., Identification of a Novel Major Histocompatibility Complex Class II—restricted Tumor Antigen Resulting from a

(56) References Cited

OTHER PUBLICATIONS

Chromosomal Rearrangement Recognized by CD4+ T Cells. J Exp Med. May 17, 1999;189(10):1659-1668.
Weaver et al., Genetic determinants of Venezuelan equine encephalitis emergence. Arch Virol Suppl. 2004;(18):43-64.
Weaver et al., Venezuelan Equine Encephalitis. Annu Rev Entomol. 2004;49:141-174.
Wentworth et al., An Influenza A (HINI) Virus, Closely Related to Swine Influenza Virus, Responsible for a Fatal Case of Human Influenza. J Virol. Apr. 1994;68(4):2051-2058.
Wille-Reece et al., HIV Gag protein conjugated to a Toll-like receptor 7/8 agonist improves the magnitude and quality of Th1 and CD8+ T cell responses in nonhuman primates. Proc Natl Acad Sci U S A. Oct. 18, 2005;102(42):15190-15194.
Wille-Reece et al., Immunization with HIV-1 Gag Protein Conjugated to a TLR7/8 Agonist Results in the Generation of HIV-1 Gag-Specific Th1 and CD8+ T Cell Responses. J Immunol. Jun. 15, 2005;174(12):7676-7683.
Wille-Reece et al., Toll-like receptor agonists influence the magnitude and quality of memory T cell responses after prime-boost immunization in nonhuman primates. J Exp Med. May 15, 2006;203(5):1249-1258.
Woycechowsky and Raines, Native Disulfide Bond Formation in Proteins. Curr Opin Chem Biol. Oct. 2000;4(5):533-539.
Yi et al., Single Nucleotide Polymorphisms of Human STING Can Affect Innate Immune Response to Cyclic Dinucleotides. PLoS One. Oct. 21, 2013;8(10):e77846.
Yin et al., Cyclic di-GMP Sensing via the Innate Immune Signaling Protein STING. Mol Mol Cell. Jun. 29, 2012;46(6):735-745.
Zaremba et al., Identification of an Enhancer Agonist Cytotoxic T Lymphocyte Peptide from Human Carcinoembryonic Antigen. Cancer Res. Oct. 15, 1997;57(20):4570-4577.
Zeier et al., New Ecological Aspects of Hantavirus Infection: A Change of a Paradigm and a Challenge of Prevention—A Review. Virus Genes. Mar. 2005;30(2):157-180.
Zhang et al., c-di-GMP Displays a Monovalent Metal Ion-Dependent Polymorphism. J Am Chem Soc. Dec. 29, 2004;126(51):16700-16701.
Zhao et al., Thiophosphate Analogs of c-di-GMP: Impact on Polymorphism. Nucleosides Nucleotides Nucleic Acids. May 2009;28(5):352-378.
Zhou et al., Endo-S-c-di-GMP Analogues-Polymorphism and Binding Studies with Class I Riboswitch. Molecules. Nov. 9, 2012;17(11):13376-13389.
Zhou et al., Potent suppression of c-di-GMP synthesis via I-site allosteric inhibition of diguanylate cyclases with 2'-F-c-di-GMP. Bioorg Med Chem. Jul. 15, 2013;21(14):4396-4404.
Zimmerman et al., Expression of annexin II in conventional renal cell carcinoma is correlated with Fuhrman grade and clinical outcome. Virchows Arch. Oct. 2004;445(4):368-374.
Ziyaeyan et al., The Seroprevalence of Parvovirus BI9 Infection among To-Be-Married Girls, Pregnant Women, and Their Neonates in Shi raz, Iran. Jpn J Infect Dis. Apr. 2005;58(2):95-97.
Havlasova et al., Mapping of immunoreactive antigens of Francisella tularensis live vaccine strain. Proteomics. Jul. 2002;2(7):857-867.
Havlasova et al., Proteomic analysis of anti-Francisella tularensis LVS antibody response in murine model of tularemia. Proteomics. May 2005;5(8):2090-2103.
Hayakawa, A facile synthesis of cyclic bis(30!50)diguanylic acid. Tetrahedron 2003;59:6465-6471.
He et al., Complexes of Poliovirus Serotypes with Their Common Cellular Receptor, CD155. J Virol. Apr. 2003;77(8):4827-4835.
Hirose et al., Incidence of Diffuse Large B-Cell Lymphoma of Germinal Center B-Cell Origin in Whole Diffuse Large B-Cell Lymphoma: Tissue Fluorescence in Situ Hybridization Using t(14;18) Compared with Immunohistochemistry. Int J Hematol. Jan. 2005;81(1):48-57.

Hoffman et al., Strategy for development of a pre-erythrocytic Plasmodium falciparum DNA vaccine for human use. Vaccine. Jun. 1997;15(8):842-845.
Hoke, History of U.S. Military Contributions to the Study of Viral Encephalitis. Mil Med. Apr. 2005;170(4 Suppl):92-105.
Hu et al., c-di-GMP as a vaccine adjuvant enhances protection against systemic methicillin-resistant *Staphylococcus aureus* (MRSA) infection. Vaccine. Jul. 30, 2009;27(35):4867-4873.
Hughes, Nanostructure-mediated drug delivery. Nanomedicine. Mar. 2005;1(1):22-30.
Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.
Hutchinson et al., Multiplex Analysis of Cytokines in the Blood of Cynomolgus Macaques Naturally Infected With Ebola Virus (Reston Serotype). J Med Virol. Nov. 2001;65(3):561-566.
Hyodo et al., Synthesis of cyclic bis(3'-5')diguanylic acid (c-di-GMP) analogs. Tetrahedron 2006;62:3089-3094.
Iacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 15, 2003;63(24):8614-8622.
Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.
Isherwood et al., Vaccination strategies for Francisella tularensis. Adv Drug Deliv Rev. Jun. 17, 2005;57(9):1403-1414.
Ishikawa and Barber, Sting an Endoplasmic Reticulum Adaptor that Facilitates Innate Immune Signaling. Nature. Oct. 2, 2008;455(7213):674-678.
Ito et al., Prostate Carcinoma Detection and Increased Prostate-Specific Antigen Levels after 4 Years in Dutch and Japanese Males Who Had No Evidence of Disease at Initial Screening. Cancer. Jan. 15, 2005;103(2):242-250.
Iwasaki and Medzhitov, Regulation of adaptive immunity by the innate immune system. Science. Jan. 15, 2010;327(5963):291-295.
Jainkittivong and Langlais, Herpes B virus infection. Oral Surg Oral Med Oral Pathol Oral Radiol Endod. Apr. 1998;85(4):399-403.
Jamieson et al., Human Torovirus: A New Nosocomial Gastrointestinal Pathogen. J Infect Dis. Nov. 1998;178(5):1263-1269.
Jansen and Shaw, Human Papillomavirus Vaccines and Prevention of Cervical Cancer. Annu Rev Med. 2004;55:319-331.
Jin et al., Identification and characterization of a loss-of-function human MPYS variant. Genes Immun. Jun. 2011;12(4):263-269.
Jung et al., Strategies Against Human Papillomavirus Infection and Cervical Cancer. J Microbiol. Dec. 2004;42(4):255-266.
Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.
Karaolis et al., Bacterial c-di-GMP Is an Immunostimulatory Molecule. J Immunol. Feb. 15, 2007;178(4):2171-2181.
Karaolis et al., Cyclic Di-GMP Stimulates Protective Innate Immunity in Bacterial Pneumonia. Infect Immun. Oct. 2007;75(10):4942-4950.
Kaufman et al., Parvovirus B19 does not bind to membrane-associated globoside in vitro. Virology. Feb. 5, 2005;332(1):189-198.
Kawai and Akira, The role of pattern-recognition receptors in innate immunity: update on Toll-like receptors. Nat Immunol. May 2010;11(5):373-384.
Kedl et al., Comparative Sequence Analysis of the Reovirus S4 Genes from 13 Serotype 1 and Serotype 3 Field Isolates. J Virol. Jan. 1995;69(1):552-559.
Kim et al., Co-Crystal Structures of PKG 1β (92-227) with cGMP and cAMP Reveal the Molecular Details of Cyclic-Nucleotide Binding. PLoS One. Apr. 19, 2011;6(4):e18413.
Kim et al., Comparison of HPV DNA vaccines employing intracellular targeting strategies. Gene Ther. Jun. 2004;11(12):1011-1018.

(56) References Cited

OTHER PUBLICATIONS

Krzych et al., T lymphocytes from volunteers immunized with irradiated Plasmodium falciparum sporozoites recognize liver and blood stage malaria antigens. J Immunol. Oct. 15, 1995;155(8):4072-4077.
Kubuschok et al., Expression of cancer testis antigens in pancreatic carcinoma cell lines, pancreatic adenocarcinoma and chronic pancreatitis. Int J Cancer. Apr. 20, 2004;109(4):568-575.
Kumamuru et al., T-cell receptor Vbeta gene usage by T cells reactive with the tumor-rejection antigen SART-1 in oral squamous cell carcinoma. Int J Cancer. Feb. 20, 2004;108(5):686-695.
Laheru and Jaffee, Immunotherapy for pancreatic cancer—science driving clinical progress. Nat Rev Cancer. Jun. 2005;5(6):459-467.
Lauvau et al., Priming of Memory But Not Effector CD8 T Cells by a Killed Bacterial Vaccine. Science. Nov. 23, 2001;294(5547):1735-1739.
Lee et al., A clinical grade cocktail of cytokines and PGE2 results in uniform maturation of human monocyte-derived dendritic cells: implications for immunotherapy. Vaccine. Dec. 19, 2002;20 Suppl 4:A8-A22.
Lee et al., Immunomic analysis of human sarcoma. Proc Natl Acad Sci U S A. Mar. 4, 2003;100(5):2651-2656.
Li et al., Advanced Glycation End Products Induce Tubular Epithelial-Myofibroblast Transition through the RAGE-ERK1/2 MAP Kinase Signaling Pathway. Am J Pathol. Apr. 2004;164(4):1389-1397.
Li et al., Expression Profile of Cancer-Testis Genes in 121 Human Colorectal Cancer Tissue and Adjacent Normal Tissue. Clin Cancer Res. Mar. 1, 2005;11(5):1809-1814.
Liang et al., Microvessel density, cyclo-oxygenase 2 expression, K-ras mutation and p53 overexpression in colonic cancer. Br J Surg. Mar. 2004;91(3):355-361.
Libanova et al., The member of the cyclic di-nucleotide family bis-(3', 5')-cyclic dimeric inosine monophosphate exerts potent activity as mucosal adjuvant. Vaccine. Mar. 2, 2010;28(10):2249-2258.
Lim et al., Molecular and phenotypic spectrum of de novo Philadelphia positive acute leukemia. Int J Mol Med. Dec. 1999;4(6):665-667.
Lin et al., Melanoma-Associated Antigens in Esophageal Adenocarcinoma Identification of Novel MAGE-A10 Splice Variants. Clin Cancer Res. Sep. 1, 2004;10(17):5708-5716.
Lubong Sabado et al., In Vitro Priming Recapitulates In Vivo HIV-1 Specific T Cell Responses, Revealing Rapid Loss of Virus Reactive CD4+ T Cells in Acute HIV-1 Infection. PLoS One. 2009;4(1):e4256 (13 pages).
Lucas et al., MAGE-B5, MAGE-B6, MAGE-C2, and MAGE-C3: four new members of the MAGE family with tumor-specific expression. Int J Cancer. Jul. 1, 2000;87(1):55-60.
Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.
Madhun et al., Intranasal c-di-GMP-adjuvanted plant-derived H5 influenza vaccine induces multifunctional Th1 CD4+ cells and strong mucosal and systemic antibody responses in mice. Vaccine. Jul. 12, 2011;29(31):4973-4982.
Mandruzzato et al., A CASP-8 Mutation Recognized by Cytolytic T Lymphocytes on a Human Head and Neck Carcinoma. J Exp Med. Aug. 29, 1997;186(5):785-793.
Matsumoto et al., Expression of the SART-1 antigens in uterine cancers. Jpn J Cancer Res. Dec. 1998;89(12):1292-1295.
Extended European Search Report and Written Opinion issued in EP 13799826 dated Nov. 20, 2015.
Dubensky et al., Abstract 4573: A novel tumor vaccine with cyclic dinucleotides—can induce potent anti-tumor responses in vivo. Cancer Res. Apr. 15, 2013;73(8 Suppl):4573-4573.
Woodward et al.., Supporting Online Material for c-di AMP Secreted by Intracellular Listeria monocytogenes Activates a Host Type I Interferon Response. Science May 27, 2010. Retrieved online at URL:www.sciencemag.org/cgi/content/full/science.1189801/DCI on Nov. 11, 2015 (15 pages).
Fu et al., "STING agonist formulated cancer vaccines can cure established tumors resistant to PD-1 blockade", Sci Transl Med. Apr. 15, 2015;7(283):283ra52. doi: 10.1126/scitranslmed.aaa4306.
Pardoll, Drew, "The blockade of immune checkpoints in cancer immunotherapy", Nat Rev Cancer. Mar. 22, 2012;12(4):252-64. doi: 10.1038/nrc3239.
Abutaily et al., Cadherins, catenins and APC in pleural malignant mesothelioma. J Pathol. Nov. 2003;201(3):355-362.
Aguilar et al., Endemic Venezuelan Equine Encephalitis in Northern Peru. Emerg Infect Dis. May 2004;10(5):880-888.
Ahn et al., All CVB Serotypes and Clinical Isolates Induce Irreversible Cytopathic Effects in Primary Cardiomyocytes. J Med Virol. Feb. 2005;75(2):290-294.
Altwein and Luboldt, Prognostic Factors for Carcinoma of the Prostate. Urol Int. 1999:63(1):62-71.
Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. May 2005;64(5):780-782.
Andersen and thor Straten, Survivin—a universal tumor antigen. Histol Histopathol. Apr. 2002;17(2):669-675.
Argani et al., Discovery of New Markers of Cancer through Serial Analysis of Gene Expression Prostate Stem Cell Antigen Is Overexpressed in Pancreatic Adenocarcinoma. Cancer Res. Jun. 1, 2001;61(11):4320-4324.
Arora et al., Identification of Differentially Expressed Genes in Oral Squamous Cell Carcinoma. Mol Carcinog. Feb. 2005;42(2):97-108.
Attoui et al., Comparative sequence analysis of American, European and Asian isolates of viruses in the genus *Coltivirus*. J Gen Virol. Oct. 1998;79 ( Pt 10):2481-2489.
Badovinac et al., Accelerated CD8+ T-cell memory and prime-boost response after dendritic-cell vaccination. Nat Med. Jul. 2005;11(7):748-756.
Bahjat et al., Suppression of Cell-Mediated Immunity following Recognition of Phagosome-Confined Bacteria. PLoS Pathog. Sep. 2009;5(9):e1000568.
Bala et al., PLGA Nanoparticles in Drug Delivery: The State of the Art. Crit Rev Ther Drug Carrier Syst. 2004;21(5):387-422.
Baldwin et al., The Importance of Adjuvant Formulation in the Development of a Tuberculosis Vaccine. J Immunol. Mar. 1, 2012;188(5):2189-2197.
Barbanti-Brodano et al., Simian virus 40 infection in humans and association with human diseases: results and hypotheses. Virology. Jan. 5, 2004;318(1):1-9.
Barber, Cytoplasmic DNA innate immune pathways. Immunol Rev. Sep. 2011;243(1):99-108.
Barthold et al., Infectivity, disease patterns, and serologic profiles of reovirus serotypes 1, 2, and 3 in infant and weanling mice. Lab Anim Sci. Oct. 1993;43(5):425-430.
Battistini et al., Stereoselective Synthesis of Cyclic Dinucleotide Phosphorothioates. Tetrahedron, 1993;49(5):1115-1132.
Baurain et al., High Frequency of Autologous Anti-Melanoma CTL Directed Against an Antigen Generated by a Point Mutation in a New Helicase Gene. J Immunol. Jun. 1, 2000;164(11):6057-6066.
Bevanger et al., Competitive Enzyme Immunoassay for Antibodies to a 43,000-Molecular-Weight Francisella tularensis Outer Membrane Protein for the Diagnosis of Tularemia. J Clin Microbiol. May 1989;27(5):922-926.
Bhigjee et al., Sequence of the env gene of some KwaZulu-Natal, South African strains of HTLV type I. Aids Res Hum Retroviruses. Sep. 1, 1999;15(13):1229-1233.
Biagini et al., Simultaneous measurement of specific serum IgG responses to five select agents. Anal Bioanal Chem. Jun. 2005;382(4):1027-1034.
Bondurant et al., Definition of an Immunogenic Region Within the Ovarian Tumor Antigen Stratum Corneum Chymotryptic Enzyme. Clin Cancer Res. May 1, 2005;11(9):3446-3454.
Brezniceanu et al., HMGB1 inhibits cell death in yeast and mammalian cells and is abundantly expressed in human breast carcinoma. FASEB J. Jul. 2003;17(10):1295-1297.

(56) References Cited

OTHER PUBLICATIONS

Brian and Baric, Coronavirus Genome Structure and Replication. Curr Top Microbiol Immunol. 2005;287:1-30.

Brinkmann et al., Novel Genes in the PAGE and GAGE Family of Tumor Antigens Found by Homology Walking in the dbEST Database. Cancer Res. Apr. 1, 1999;59(7):1445-1448.

Brockstedt et al., Killed but metabolically active microbes: a new vaccine paradigm for eliciting effector T-cell responses and protective immunity. Nat Med. Aug. 2005;11(8):853-860.

Bronte et al., Genetic Vaccination with "Self" Tyrosinase-related Protein 2 Causes Melanoma Eradication but not Vitiligo. Cancer Res. Jan. 15, 2000;60(2):253-258.

Brown et al., Complete Genomic Sequencing Shows that Polioviruses and Members of Human Enterovirus Species C Are Closely Related in the Noncapsid Coding Region. J Virol. Aug. 2003;77(16):8973-8984.

Brown, Variants of B19. Dev Biol (Basel). 2004;118:71-77.

Burdette and Vance, STING and the innate immune response to nucleic acids in the cytosol. Nat Immunol. Jan. 2013;14(1):19-26.

Burdette et al., STING is a direct innate immune sensor of cyclic di-GMP. Nature. Sep. 25, 2011;478(7370):515-518 doi:10.1038/nature10429.

Capdepont et al., New Insights in HTLV-I Phylogeny by Sequencing and Analyzing the Entire Envelope Gene. AIDS Res Hum Retroviruses. Jan. 2005;21(1):28-42.

Capurro et al., Glypican-3: A Novel Serum and Histochemical Marker for Hepatocellular Carcinoma. Gastroenterology. Jul. 2003;125(1):89-97.

Carbone et al., New developments about the association of SV40 with human mesothelioma. Oncogene. Aug. 11, 2003;22(33):5173-5180.

Chan et al., In Situ Hybridization Study of PSP94 (Prostatic Secretory Protein of 94 Amino Acids) Expression in Human Prostates. Prostate. Oct. 1, 1999;41(2):99-109.

Chang et al., A Phase I Trial of Tumor Lysate-Pulsed Dendritic Cells in the Treatment of Advanced Cancer. Clin Cancer Res. Apr. 2002;8(4):1021-1032.

Chen et al., Immunodominant CD41 responses identified in a patient vaccinated with full-length NY-ESO-1 formulated with ISCOMATRIX adjuvant. Proc Natl Acad Sci USA. Jun. 22, 2004;101(25):9363-9368.

Chern et al., Glycoprotein B Subtyping of Cytomegalovirus (CMV) in the Vitreous of Patients with AIDS and CMV Retinitis. J Infect Dis. Oct. 1998;178(4):1149-1153.

Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.

Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.

Clements et al., Adenomatous Polyposis Coli/β-Catenin Interaction and Downstream Targets: Altered Gene Expression in Gastrointestinal Tumors. Clin Colorectal Cancer. Aug. 2003;3(2):113-120.

Clifton et al., A chlamydial type III translocated protein is tyrosine-phosphorylated at the site of entry and associated with recruitment of actin. Proc Nati Acad Sci USA. Jul. 6, 2004;101(27):10166-10171.

Clinton et al., A Comparative Study of Four Serological Tumor Markers for the Detection of Breast Cancer. Biomed Sci Instrum. 2003;39:408-414.

Cobaleda et al., A primitive hematopoietic cell is the target for the leukemic transformation in human Philadelphia-positive acute lymphoblastic leukemia. Blood. Feb. 1, 2000;95(3):1007-1013.

Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.

Coler et al. Development and Characterization of Synthetic Glucopyranosyl Lipid Adjuvant System as a Vaccine Adjuvant. PLoS One. Jan. 26, 2011;6(1):e16333.

Search Report and Written Opinion issued by IPOS in Singapore patent application No. 11201407875U dated Sep. 15, 2015.

Coughlin et al., Orally Bioavailable Anti-HBV Dinucleotide Acyloxyalkyl Prodrugs. Bioorg Med Chem Lett. Mar. 1, 2010;20(5):1783-1786.

Creighton et al., Mechanisms and catalysts of disulfide bond formation in proteins. Trends Biotechnol. Jan. 1995;13(1):18-23.

Dalerba et al., MAGE, BAGE and GAGE gene expression in human rhabdomyosarcomas. Int J Cancer. Jul. 1, 2001;93(1):85-90.

Damasus-Awatai and Freeman-Wang, Human papilloma virus and cervical screening. Curr Opin Obstet Gynecol. Dec. 2003;15(6):473-477.

Das et al., Evaluation of a Western Equine Encephalitis recombinant E1 protein for protective immunity and diagnostics. Antiviral Res. Nov. 2004;64(2):85-92.

Davies et al., Characterisation of a recombinant Fv fragment of anti-MUC1 antibody HMFG1. Cancer Lett. Jul. 29, 1994;82(2):179-184.

Davies et al., Coordinated Regulation of Accessory Genetic Elements Produces Cyclic Di-Nucleotides for V. cholerae Virulence. Cell. Apr. 13, 2012;149(2):358-370.

De Backer et al., Characterization of the GAGE Genes That Are Expressed in Various Human Cancers and in Normal Testis. Cancer Res. Jul. 1, 1999;59(13):3157-3165.

De Villiers et al., Classification of papillomaviruses. Virology. Jun. 20, 2004;324(1):17-24.

Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64(10):3653-3660.

Desmet and Ishii, Nucleic acid sensing at the interface between innate and adaptive immunity in vaccination. Nat Rev Immunol. Jun. 22, 2012;12(7):479-491.

Dessureault et al., A phase-I Trial Using a Universal GM-CSF-producing and CD40L-expressing Bystander Cell Line (GM.CD40L) in the Formulation of Autologous Tumor Cell-based Vaccines for Cancer Patients with Stage IV disease. Ann Surg Oncol. Feb. 2007;14(2):869-884.

Diner et al., The Innate Immune DNA Sensor cGAS Produces a Noncanonical Cyclic Dinucleotide that Activates Human STING. Cell Rep. May 30, 2013;3(5):1355-1361.

Disis and Cheever, HER-2/Neu Protein: A Target for Antigen-Specific Immunotherapy of Human Cancer. Adv Cancer Res. 1997;71:343-371.

Disis et al., Humoral Epitope-Spreading Following Immunization with a HER-2/neu Peptide Based Vaccine in Cancer Patients. J Clin Immunol. Sep. 2004;24(5):571-578.

Dosaka-Akita et al., Expression of N-Acetylglucosaminyltransferase V Is Associated with Prognosis and Histology in Non-Small Cell Lung Cancers. Clin Cancer Res. Mar. 1, 2004;10(5):1773-1779.

Duxbury et al., CEACAM6 as a novel target for indirect type 1 immunotoxin-based therapy in pancreatic adenocarcinoma. Biochem Biophys Res Commun. May 7, 2004;317(3):837-843.

Ebensen et al., Bis-(3',5')-cyclic dimeric adenosine monophosphate: Strong Th1/Th2/Th17 promoting mucosal adjuvant. Vaccine. Jul. 18, 2011;29(32):5210-5220.

Ebensen et al., The bacterial second messenger cyclic diGMP exhibits potent adjuvant properties. Vaccine. Feb. 9, 2007;25(8):1464-1469.

Ebensen et al., The Bacterial Second Messenger cdiGMP Exhibits Promising Activity as a Mucosal Adjuvant. Clin Vaccine Immunol. Aug. 2007;14(8):952-958.

Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbiol. May 1997;35(5):1122-1130.

(56) References Cited

OTHER PUBLICATIONS

Engels et al., Serologic Evidence for Exposure to Simian Virus 40 in North American Zoo Workers. J Infect Dis. Dec. 15, 2004;190(12):2065-2069.
Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.
Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.
Estrada-Franco et al., Venezuelan Equine Encephalitis Virus, Southern Mexico. Emerg Infect Dis. Dec. 2004;10(12):2113-2121.
Fang et al., Expression of Dnmt1, demethylase, MeCP2 and methylation of tumor-related genes in human gastric cancer. World J Gastroenterol. Dec. 1, 2004;10(23)3394-3398.
Faure et al., Inducible Hsp70 as Target of Anticancer Immunotherapy: Identification of HLA-A*0201-Restricted Epitopes. Int J Cancer. Mar. 1, 2004;108(6):863-870.
Fleishhauer et al., The DAM Gene Family Encodes a New Group of Tumor-specific Antigens Recognized by Human Leukocyte Antigen Al-restricted Cytotoxic T Lymphocytes. Cancer Res. Jul. 15, 1998;58(14):2969-2972.
Fong et al., Altered peptide ligand vaccination with Flt3 ligand expanded dendritic cells for tumor immunotherapy. Proc Natl Acad Sci U S A. Jul. 17, 2001;98(15):8809-8814.
Fuessel et al., Multiple tumor marker analyses (PSA, hK2, PSCA, trp-p8) in primary prostate cancers using quantitative RT-PCR. Int J Oncol. Jul. 2003;23(1):221-228.
Fujii et al., The VesiVax system: a method for rapid vaccine development. Front Biosci. Jan. 1, 2008;13:1968-1980.
Gaffney et al., One-Flask Syntheses of c-di-GMP and the [Rp,Rp] and [Rp,Sp] Thiophosphate Analogues. Org Lett. Jul. 16, 2010;12(14):3269-3271.
Gambus et al., Epitope mapping of a mouse monoclonal anti-MUC2 antibody suggests the existence of an immunodominant region in the COOH terminus of the MUC2 tandem-repeat sequence. Int J Cancer. Jan. 3, 1995;60(1):146-148.
Gao et al., Cyclic [G(20,50)pA(30,50)p] Is the Metazoan Second Messenger Produced by DNA-Activated Cyclic GMP-AMP Synthase. Cell. May 23, 2013;153(5):1094-1107.
Gao et al., Structure-Function Analysis of STING Activation by c[G(2',5')pA(3',5')p] and Targeting by Antiviral DMXAA. Cell. Aug. 15, 2013;154(4):748-762.
Geisbert and Jahrling, Differentiation of filoviruses by electron microscopy. Virus Res. Dec. 1995;39(2-3):129-150.
Ghazizadeh et al., Role of cdk4, p16INK4, and Rb Expression in the Prognosis of Bronchioloalveolar Carcinomas. Respiration. Jan.-Feb. 2005;72(1):68-73.
Gilliam et al., A phase II study of G17DT in gastric carcinoma. Eur J Surg Oncol. Jun. 2004;30(5):536-543.
Gonzalez et al., A comparative sequence analysis to revise the current taxonomy of the family Coronaviridae. Arch Virol. Nov. 2003;148(11):2207-2235.
Good et al., Development and regulation of cell-mediated immune responses to the blood stages of malaria: implications for vaccine research. Annu Rev Immunol. 2005;23:69-99.
Good et al., The immunological challenge to developing a vaccine to the blood stages of malaria parasites. Immunol Rev. Oct. 2004;201:254-267.
Grajkowski et al., Convenient Synthesis of a Propargylated Cyclic (3'-5') Diguanylic Acid and its "Click" Conjugation to a Biotinylated Azide. Bioconjug Chem. Nov. 17, 2010;21(11):2147-2152.
Grimm et al., Mouse alpha-fetoprotein-specific DNA-based immunotherapy of hepatocellular carcinoma leads to tumor regression in mice. Gastroenterology. Oct. 2000;119(4):1104-1112.
Groh et al., Efficient cross-priming of tumor antigen-specific T cells by dendritic cells sensitized with diverse anti-MICA opsonized tumor cells. Proc Natl Acad Sci USA. May 3, 2005;102(18):6461-6466.
Gueguen et al., An Antigen Recognized by Autologous CTLs on a Human Bladder Carcinoma. J Immunol. Jun. 15, 1998;160(12):6188-6194.
Gulmann et al., Adenomatous Polyposis Coli Gene, beta-Catenin, and E-Cadherin Expression in Proximal and Distal Gastric Cancers and Precursor Lesions. Appl Immunohistochem Mol Morphol. Sep. 2003;11(3):230-237.
Gupta et al., Refolding, purification, and crystallization of apical membrane antigen 1 from Plasmodium falciparum. Protein Expr Purif. May 2005;41(1):186-198.
Haddad et al., Novel antigen identification method for discovery of protective malaria antigens by rapid testing of DNA vaccines encoding exons from the parasite genome. Infect Immun. Mar. 2004;72(3):1594-1602.
Hakansson et al., Establishment and phenotypic characterization of human U937 cells with inducible P210 BCR/ABL expression reveals upregulation of CEACAM1 (CD66a). (2004) Leukemia 18:538-547.
Harris et al., The Biological and Therapeutic Importance of Gastrin Gene Expression in Pancreatic Adenocarcinomas. Cancer Res. Aug. 15, 2004;64(16):5624-5631.
Harty and Badovinac, Shaping and reshaping CD8+ T-cell memory. Nat Rev Immunol. Feb. 2008;8(2):107-19-119.
Hashido et al., Evaluation of an Enzyme-Linked Immunosorbent Assay Based on Binding Inhibition for Type-Specific Quantification of Poliovirus Neutralization-Relevant Antibodies. Microbiol Immunol. 1999;43(1):73-77.
Hassan et al., Mesothelin: A New Target for Immunotherapy. Clin Cancer Res. Jun. 15, 2004;10(12 Pt 1):3937-3942.
Adams et al., PHENIX: a comprehensive Python-based system for macromolecular structure solution. Acta Crystallogr D Biol Crystallogr. Feb. 2010;66(Pt 2):213-221.
Baguley and Ching, DMXAA: An antivascular agent with multiple host responses. Int J Radiat Oncol Biol Phys. Dec. 1, 2002;54(5)1503-1511.
Burckstummer et al., An orthogonal proteomic-genomic screen identifies AIM2 as a cytoplasmic DNA sensor for the inflammasome. Nat Immunol. Mar. 2009;10(3):266-272.
Cai et al., The cGAS-cGAMP-STING Pathway of Cytosolic DNA Sensing and Signaling. Mol Cell. Apr. 24, 2014;54(2):289-296.
Cavlar et al., Species-specific detection of the antiviral small-molecule compound CMA by STING. EMBO J. May 15, 2013;32(10):1440-1450.
The International Search Report and Written Opinion issued in PCTUS2014035909 dated Sep. 12, 2014.
The International Search Report and Written Opinion issued in PCTUS2014049140 dated Dec. 22, 2014.
Dai et al., Modified Vaccinia Virus Ankara Triggers Type I IFN Production in Murine Conventional Dendritic Cells via a cGAS/STING-Mediated Cytosolic DNA-Sensing Pathway. PLoS Pathog. Apr. 17, 2014;10(4):e1003989.
Donovan et al., Structural basis for cytosolic double-stranded RNA surveillance by human oligoadenylate synthetase 1. Proc Natl Acad Sci U S A. Jan. 29, 2013;110(5):1652-1657 plus 12 pages Supporting Information—(18 pages ttl).
Egli et al., Atomic-resolution structure of the cellulose synthase regulator cyclic diguanylic acid. Proc Natl Acad Sci U S A. Apr. 1990;87(8):3235-3239.
Ekins et al., In silico pharmacology for drug discovery: methods for virtual ligand screening and profiling. Br J Pharmacol. Sep. 2007;152(1):9-20.
Emsley et al., Features and development of Coot. Acta Crystallogr D Biol Crystallogr. Apr. 2010;66(Pt 4):486-501.
Fernandes-Alnemri et al., AIM2 activates the inflammasome and cell death in response to cytoplasmic DNA. Nature. Mar. 26, 2009;458(7237):509-513.
Gaffney and Jones, One-flask syntheses of cyclic diguanosine monophosphate (c-di-GMP). Curr Protoc Nucleic Acid Chem. Mar. 2012;Chapter 14:Unit 14.8.1-7.
Gall et al., Autoimmunity Initiates in Nonhematopoietic Cells and Progresses via Lymphocytes in an Interferon-Dependent Autoimmune Disease. Immunity. Jan. 27, 2012;36(1):120-131.

(56) References Cited

OTHER PUBLICATIONS

Gao et al., Binding-Pocket and Lid-Region Substitutions Render Human STING Sensitive to the Species-Specific Drug DMXAA. Cell Rep. Sep. 25, 2014;8(6):1668-1676 plus 12 pages Supporting Information—(23 pages ttl).
Gehrke et al., Oxidative Damage of DNA Confers Resistance to Cytosolic Nuclease TREX1 Degradation and Potentiates STING-Dependent Immune Sensing. Immunity. Sep. 19, 2013;39(3):482-495.
Hartmann et al., Crystal Structure of the 2'-Specific and Double-Stranded RNA-Activated Interferon-Induced Antiviral Protein 2'-5'-Oligoadenylate Synthetase. Mol Cell. Nov. 2003;12(5):1173-1185.
Head and Jameson, The development of the tumor vascular-disrupting agent ASA404 (vadimezan, DMXAA): current status and future opportunities. Expert Opin Investig Drugs. Feb. 2010;19(2):295-304.
Higashida et al., Measurement of adenylyl cyclase by separating cyclic AMP on silica gel thin-layer chromatography. Anal Biochem. Sep. 1, 2002;308(1):106-111.
Hornung and Latz, Intracellular DNA recognition. Nat Rev Immunol. Feb. 2010;10(2):123-130.
Hornung et al., AIM2 recognizes cytosolic dsDNA and forms a caspase-1-activating inflammasome with ASC. Nature. Mar. 26, 2009;458(7237):514-518.
Huang et al., The structural basis for the sensing and binding of cyclic di-GMP by STING. Nat Struct Mol Biol. Jun. 24, 2012;19(7):728-30—Supplementary Information only (5 pages).
Huffman and Brennan, Prokaryotic transcription regulators: more than just the helix-turn-helix motif. Curr Opin Struct Biol. Feb. 2002;12(1):98-106.
Jin et al., MPYS, a Novel Membrane Tetraspanner, Is Associated with Major Histocompatibility Complex Class II and Mediates Transduction of Apoptotic Signals. Mol Cell Biol. Aug. 2008;28(16):5014-5026 plus 9 pages Supporting Information—(22 pages ttl).
Jin et al., Structures of the HIN Domain: DNA Complexes Reveal Ligand Binding and Activation Mechanisms of the AIM2 Inflammasome and IFI16 Receptor. Immunity. Apr. 20, 2012;36(4):561-571.
Kasturi et al., Programming the magnitude and persistence of antibody responses with innate immunity. Nature 2011;470:543-547.
Keating et al., Cytosolic DNA sensors regulating type I interferon induction. Trends Immunol. Dec. 2011;32(12):574-581.
Kerur et al., IFI16 Acts as a Nuclear Pathogen Sensor to Induce the Inflammasome in Response to Kaposi Sarcoma-Associated Herpesvirus Infection. Cell Host Microbe. May 19, 2011;9(5):363-375.
Kodym et al., 2'-5'-Oligoadenylate synthetase is activated by a specific RNA sequence motif. Biochem Biophys Res Commun. Oct. 16, 2009;388(2):317-322.
Krasteva et al., Sensing the messenger: The diverse ways that bacteria signal through c-di-GMP. Protein Sci. Jul. 2012;21(7):929-948.
Kubota et al., Identification of 2'-Phosphodiesterase, Which Plays a Role in the 2-5A System Regulated by Interferon. J Biol Chem. Sep. 3, 2004;279(36):37832-37841.
Kulshina et al., Recognition of the bacterial second messenger cyclic diguanylate by its cognate riboswitch. Nat Struct Mol Biol. Dec. 2009;16(12):1212-1217.
Lara Jr. et al., Randomized Phase III Placebo-Controlled Trial of Carboplatin and Paclitaxel With or Without the Vascular Disrupting Agent Vadimezan (ASA404) in Advanced Non-Small-Cell Lung Cancer. J Clin Oncol. Aug. 1, 2011;29(22):2965-2971.
Lee et al., An Allosteric Self-Splicing Ribozyme Triggered by a Bacterial Second Messenger. Science. Aug. 13, 2010;329(5993):845-848.
Lunde et al., RNA-binding proteins: modular design for efficient function. Nat Rev Mol Cell Biol. Jun. 2007;8(6):479-490.
McCoy et al., Phaser crystallographic software. J Appl Crystallogr. Aug. 1, 2007;40(Pt 4):658-674.
Murshudov et al., Refinement of Macromolecular Structures by the Maximum-Likelihood Method. Acta Crystallogr D Biol Crystallogr. May 1, 1997;53(Pt 3):240-255.
Otwinowski and Minor, Processing of X-ray Diffraction Data Collected in Oscillation Mode. Methods Enzymol. 1997;276:307-326.
Paludan and Bowie, Immune Sensing of DNA. Immunity. May 23, 2013;38(5):870-880.
Porter et al., Merck Manual of Diagnosis and Therapy, 19th Edition. Merck Sharp & Dohme Corp., A Subsidiary of Merck & Co., Inc. Copyright: © Merck Manuals Aug. 1, 2011:1059-1062.
Rasmussen et al., Activation of Autophagy by α-Herpesviruses in Myeloid Cells Is Mediated by Cytoplasmic Viral DNA through a Mechanism Dependent on Stimulator of IFN Genes. J Immunol. Nov. 15, 2011;187(10):5268-5276.
Roberts et al., IFN-β-Dependent Inhibition of Tumor Growth by the Vascular Disrupting Agent 5,6- Dimethylxanthenone-4-Acetic Acid (DMXAA). J Interferon Cytokine Res. Mar. 2008;28(3):133-139.
Ross et al., Regulation of cellulose synthesis in Acetobacter xylinum by cyclic diguanylic acid. Nature. Jan. 15-21, 1987;325(6101):279-281.
Sadler and Williams, Interferon-inducible antiviral effectors. Nat Rev Immunol. Jul. 2008;8(7):559-568.
Schirmer and Jenal, Structural and mechanistic determinants of c-di-GMP signalling. Nat Rev Microbial. Oct. 2009;7(10):724-735.
Schoggins et al., A diverse range of gene products are effectors of the type I interferon antiviral response. Nature. Apr. 28, 2011;472(7344):481-485.
Shang et al., Crystal structures of STING protein reveal basis for recognition of cyclic di-GMP. Nat Struct Mol Biol. Jun. 24, 2012;19(7):725-727.
Smith et al., Structural basis of ligand binding by a c-di-GMP riboswitch. Nat Struct Mol Biol. Dec. 2009;16(12):1218-1223.
Sudarsan et al., Riboswitches in Eubacteria Sense the Second Messenger Cyclic Di-GMP. Science. Jul. 18, 2008;321(5887):411-413.
Sun et al., ERIS, an endoplasmic reticulum IFN stimulator, activates innate immune signaling through dimerization. Proc Natl Acad Sci U S A. May 26, 2009;106(21):8653-8658—plus 6 pages Supporting Information—(12 pp ttl).
Venes et al., Taber's Cyclopedic Medical Dictionary, Ed. 21. F.A. Davis Co., Philadelphia, Copyright: © 2009:1163.
Wolkowicz and Cook, NF45 dimerizes with NF90, Zfr and SPNR via a conserved domain that has a nucleotidyltransferase fold. Nucleic Acids Res. Oct. 2012;40(18):9356-9368.
Xiao and Fitzgerald, The cGAS-STING Pathway for DNA Sensing. Mol Cell. Jul. 25, 2013;51(2):135-139.
Yang et al., The cytosolic nucleic acid sensor LRRFIP1 mediates the production of type I interferon via a beta-catenin-dependent pathway. Nat Immunol. Jun. 2010;11(6):487-494.
Zhang et al., The helicase DDX41 senses intracellular DNA mediated by the adaptor STING in dendritic cells. Nat Immunol. Sep. 4, 2011;12(10):959-965.
Zhong et al., The Adaptor Protein MITA Links Virus-Sensing Receptors to IRF3 Transcription Factor Activation. Immunity. Oct. 17, 2008;29(4):538-550.
Ablasser et al., cGAS produces 2'-5'-linked cdn second messenger that activates STING. Nature. Jun. 20, 2013;498(7454)380-384.
Ausmees et al., Genetic data indicate that proteins containing the GGDEF domain possess diguanylate cyclase activity. FEMS Microbiol Lett. Oct. 16, 2001;204(1):163-167.
Barker et al. STING-Dependent Recognition of Cyclic di-AMP Mediates Type I Interferon Responses during Chlamydia trachomatis Infection. MBio. Apr. 30, 2013;4(3):e00018-e00013.
Bowie et al., Innate Sensing of bacterial cdns: more than just STING. Nat Immunol. Dec. 2012;13(12):1137-1139.
Burger's Medicinal Chemistry and Drug Discovery, Fifth Edition, published 1994 by Wiley-Interscience, edited by Manfred E Wolff, pp. 975-977.
Chan et al., Structural basis of activity and allosteric control of diguanylate cyclase. Proc Natl Acad Sci U S A. Dec. 7, 2004;101(49):17084-17089.

(56) References Cited

OTHER PUBLICATIONS

Chen et al., The potential of 3',5'-cyclic diguanylic acid (c-di-GMP) as an effective vaccine adjuvant. Vaccine. Apr. 19, 2010;28(18):3080-3085.
Civril et al., Structural mechanism of cytosolic DNA sensing by cGAS. Nature. Jun. 20, 2013;498(7454):332-337.
Conlon et al., Mouse, but not Human STING, Binds and Signals in Response to the Vascular Disrupting Agent 5,6-Dimethylxanthenone-4-Acetic Acid. J Immunol. May 15, 2013;190(10):5216-5225.
De Grujil et al., Whole-cell cancer vaccination: from autologous to allogeneic tumor—and dendritic cell-based vaccines. Cancer Immunol Immunother. Oct. 2008;57(10):1569-1577.
Ertem and Ferris, Synthesis of RNA oligomers on heterogeneous templates. Nature. Jan. 18, 1996;379(6562):238-240.
Ettmayer et al., Lessons Learned from Marketed and Investigational Prodrugs. J Med Chem. May 6, 2004;47(10):2393-2404.
Huang et al., The structural basis for the sensing and binding of CDG by STING. Nat Struct Mol Biol. Jun. 24, 2012;19(7):728-730.
Krishnamachari et al., Nanoparticle Delivery Systems in Cancer Vaccines. Pharm Res 2011;28:215-236.
Lam et al, Adenovirus Detection by the cGAS/STING/TBK1 DNA Sensing Cascade. J Virol. Jan. 2014;88(2):974-981.
Li et al, Cyclic GMP-AMP Synthase Is Activated by Double-Stranded DNA-Induced Oligomerization. Immunity. Dec. 12, 2013;39(6):1019-1031.
Libanova, Cyclic di-nucleotides: new era for small molecules as adjuvants. Microb Biotechnol. Mar. 2012;5(2):168-176.
Luo et al, Selective binding of 2'-F-c-di-GMP to Ct-E88 and Cb-E43, new class I riboswitches from Clostridium tetani and Clostridium botulinum respectively. Mol Biosyst. Jun. 2013;9(6):1535-1539.
Mathew et al, Cytosolic delivery of antisense oligonucleotides by listeriolysin O-containing liposomes. Gene Ther. Jul. 2003;10(13):1105-1115.
Miyabe et al., A new adjuvant delivery system 'cyclic di-GMP/YSK05 liposome' for cancer immunotherapy. J Control Release. Jun. 28, 2014;184:20-27 (author's version).
O'Neill, Immunology. Sensing the dark side of DNA. Science. Feb. 15, 2013;339(6121):763-764. Comments on Sun (herein) and Wu.
Ora et al., Hydrolytic reactions of cyclic bis(3'-5')diadenylic acid (c-di-AMP). J Physical Organic Chem. 2013; 26(3):218-225.
Parvatiyar et al., DDX41 recognizes the bacterial secondary messengers cyclic di-GMP and cyclic di-AMP to activate a type I interferon immune response. Nat Immunol. Dec. 2012;13(12):1155-1161.
Prantner et al., 5,6-Dimethylxanthenone-4-acetic Acid (DMXAA) Activates Stimulator of Interferon Gene (STING)-Dependent Innate Immune Pathways and Is Regulated by Mitochondrial Membrane Potential. J Biol Chem. Nov. 16, 2012;287(47):39776-39788.
Roembke et al., A cyclic dinucleotide containing 2-aminopurine is a general fluorescent sensor for c-di-GMP and 3',3'-cGAMP. Mol Biosyst. Jun. 2014;10(6):1568-1575.
Sawai et al., Preparation and Properties of Oligocytidylates with 2'-5' Internucleotide Linkage. Bull Chem Soc Jpn 1985;58(1):361-366.
Sawai et al., Synthesis of 2'-5' Linked Oligouridylates in Aqueous Medium Using the Pd2+ Ion. Chem Pharm Bull. 1981;29(8):2237-2245.
Shanahan et al., Identification of c-di-GMP Derivatives Resistant to an EAL Domain Phosphodiesterase. Biochemistry. Jan. 15, 2013;52(2):365-377.
Silverman, The Organic Chemistry of Drug Design and Drug Action, Published 1992 by Academic Press, pp. 352-397.
Stella, Prodrugs and Therapeutics. Expert Opinion on Therapeutic Patents 2004;14(3):277-280.
Testa et al., Prodrug Research: futile or fertile? Biochem Pharmacol. Dec. 1, 2004;68(11):2097-2106.
Tezuka et al., Synthesis of 2'-Modified Cyclic Bis(3'-5')diadenylic Acids (c-di-AMPs) and Their Promotion of Cell Division in a Freshwater Green Alga. Chem Lett. 41: 1723-25, 2012.
Tijono et al., Identification of human-selective analogues of the vascular-disrupting agent 5,6-dimethylxanthenone-4-acetic acid (DMXAA). Br J Cancer. Apr. 2, 2013;108(6):1306-1315.
Urata et al., Regio- and Diastereo-Selectivity of Montmorillonite-Catalyzed Oligomerization of Racemic Adenosine 5'-Phosphorimidazolide. Nucleosides Nucleotides Nucleic Acids. Apr. 2008;27(4):421-430.
Wu et al., Cyclic GMP-AMP Is an Endogenous Second Messenger in Innate Immune Signaling by Cytosolic DNA. Science. Feb. 15, 2013;339(6121):826-830.
Yan and Aguilar, Synthesis of 3',5'-cyclic diguanylic acid (cdiGMP) using 1-(4-chlorophenyl)-4-ethoxypiperidin-4-yl as a protecting group for 2'-hydroxy functions of ribonucleosides. Nucleosides Nucleotides Nucleic Acids. 2007;26(2):189-204.
Zhang et al., Cyclic GMP-AMP Containing Mixed Phosphodiester Linkages Is an Endogenous High-Affinity Ligand for STING. Mol Cell. Jul. 25, 2013;51(2):226-235.
Non Final Office Action issued in U.S. Appl. No. 14/106,687 dated Nov. 20, 2015.
Non Final Office Action issued in U.S. Appl. No. 14/280,667 dated Nov. 19, 2015—for 1003 & 6000.
Non Final Office Action issued in U.S. Appl. No. 14/280,668 dated Dec. 3, 2015—for 1002 & 6000.
Non Final Office Action issued in U.S. Appl. No. 14/268,967 dated Nov. 9, 2015.
International Search Report and Written Opinion issued in PCT/US2013/075189 dated Mar. 11, 2014.
International Search Report and Written Opinion issued in PCT/US2014/038525 dated Sep. 9, 2014.
International Search Report and Written Opinion issued in PCT/US2014/038526 dated Sep. 19, 2014.

\* cited by examiner

COMPOSITIONS AND METHODS FOR CANCER IMMUNOTHERAPY

The present application claims priority to U.S. Provisional Patent Application 61/657,574 filed Jun. 8, 2012, which is hereby incorporated in its entirety, including all tables, figures, and claims

BACKGROUND OF THE INVENTION

The following discussion of the background of the invention is merely provided to aid the reader in understanding the invention and is not admitted to describe or constitute prior art to the present invention.

The human immune system may generally be divided into two arms, referred to as "innate immunity" and "adaptive immunity." The innate arm of the immune system is predominantly responsible for an initial inflammatory response via a number of soluble factors, including the complement system and the chemokine/cytokine system; and a number of specialized cell types including mast cells, macrophages, dendritic cells (DCs), and natural killer cells. In contrast, the adaptive immune arm involves a delayed and a longer lasting antibody response together with CD8+ and CD4+ T cell responses that play a critical role in immunological memory against an antigen. A third arm of the immune system may be identified as involving γδ T cells and T cells with limited T cell receptor repertoires such as NKT cells and MAIT cells.

For an effective immune response to an antigen, antigen presenting cells (APCs) must process and display the antigen in a proper MHC context to a T cell, which then will result in either T cell stimulation of cytotoxic and helper T cells. Following antigen presentation successful interaction of co-stimulatory molecules on both APCs and T cells must occur or activation will be aborted. GM-CSF and IL-12 serve as effective pro-inflammatory molecules in many tumor models. For example, GM-CSF induces myeloid precursor cells to proliferate and differentiate into dendritic cells (DCs) although additional signals are necessary to activate their maturation to effective antigen-presenting cells necessary for activation of T cells. Barriers to effective immune therapies include tolerance to the targeted antigen that can limit induction of cytotoxic CD8 T cells of appropriate magnitude and function, poor trafficking of the generated T cells to sites of malignant cells, and poor persistence of the induced T cell response.

DCs that phagocytose tumor-cell debris process the material for major histocompatibility complex (MHC) presentation, upregulate expression of costimulatory molecules, and migrate to regional lymph nodes to stimulate tumor-specific lymphocytes. This pathway results in the proliferation and activation of CD4+ and CD8+ T cells that react to tumor-associated antigens. Indeed, such cells can be detected frequently in the blood, lymphoid tissues, and malignant lesions of patients.

New insights into the mechanisms underlying immune-evasion, together with combination treatment regimens that potentiate the potency of therapeutic vaccination—either directly or indirectly—through combination with immune checkpoint inhibitors or other therapies, have served as a basis for the development of vaccines that induce effective antitumor immunity.

Tumor cells genetically modified to secrete GM-CSF have been used in various strategies in an effort to generate an effective immune response to tumors, however systemic cytokine administration has not induced a direct anti-cancer response in randomized controlled trials. Irradiated GM-CSF-secreting tumor cells injected subcutaneously into patients have been shown to stimulate a local response comprising DCs, macrophages, and granulocytes. The accumulation of large numbers of APCs suggests that one function of GM-CSF in this model involved the augmentation of tumor antigen presentation. Moreover, tumor cell vaccines have shown to be safe in patients. However, the clinical efficacy of this approach has been yet to be proven.

In the context of infection, Toll-like receptor ("TLR") agonists have been shown to render dendritic cell activation immunogenic, whereas lack of TLR signaling can lead to tolerance. The implication from these studies is that localized TLR stimulation might enhance antitumor response when given as part of a combinatorial vaccine. WO2011139769 describes the formulation and use of a combined GM-CSF-secreting tumor cell (GVAX) vaccine, together with TLR4 stimulation, which reportedly provided anti-tumor efficacy in several murine models. Its efficacy in humans remains, however, to be proven.

There remains a need for improved compositions and methods for immunologic strategies to treating diseases such as cancer that can be refractory to traditional therapeutic approaches.

SUMMARY OF THE INVENTION

It is an object of the present invention to provide combination therapies for the treatment of cancer.

In a first aspect, the present invention provides compositions comprising:
one or more cyclic purine dinucleotides ("CDN") which binds to STimulator of INTerferon Gene ("STING") and induces STING-dependent TBK1 activation; and an inactivated tumor cell which expresses and secretes one or more cytokines which stimulate dendritic cell induction, recruitment and/or maturation.

As described hereinafter, a number of CDNs find use in the present invention. Preferred cyclic purine dinucleotides include, but are not limited to, one or more of c-di-AMP, c-di-GMP, c-di-IMP, c-AMP-GMP, c-AMP-IMP, c-GMP-IMP, and analogs thereof. This list is not meant to be limiting.

Similarly, preferred costimulatory agent comprises one or more cytokines which stimulate dendritic cell induction, recruitment, and/or maturation include, but are not limited to, one or more of GM-CSF, CD40 ligand, IL-12, CCL3, CCL20, and CCL21. This list is not meant to be limiting.

The compositions of the present invention may be administered to individuals in need thereof by a variety of parenteral and nonparenteral routes in formulations containing pharmaceutically acceptable carriers, adjuvants and vehicles. Preferred routes are parenteral, and include but, are not limited to, one or more of subcutaneous, intravenous, intramuscular, intraarterial, intradermal, intrathecal and epidural administrations. Particularly preferred is administration by subcutaneous administration. Preferred pharmaceutical composition are formulated as aqueous or oil-in-water emulsions.

The compositions of the present invention may comprise, or be administered together with, one or more additional pharmaceutically active components such as adjuvants, lipids such as digitonin, liposomes, CTLA-4 and PD-1 pathway Antagonists, PD-1 pathway blocking agents, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-1-like receptors (RLRs), C-type lectin receptors (CLRs), pathogen-associated molecular patterns ("PAMPs"), chemotherapeutic agents, etc.

As described hereinafter, cyclic purine dinucleotides formulated with one or more lipids can exhibit improved properties, including improved dendritic cell activation activity. Thus, the present invention also relates to a composition comprising one or more CDNs and one or more lipids. In certain preferred embodiments, one or more CDNs are formulated with digitonin, a liposomal formulation, and/or an oil-in-water emulsion. While these formulations of the invention may be administered without an inactivated tumor cell which expresses and secretes one or more cytokines which stimulate dendritic cell induction, recruitment and/or maturation, in certain embodiments, the formulation of CDNs with one or more lipids are provided together with one or more such cell lines.

In related aspects, the present invention relates to methods for inducing an immune response to a cancer in an individual. These methods comprise administering a composition according to the present invention to an individual in need thereof, wherein the inactivated tumor cell or a mixture of different tumor cells are type-matched to the individual's cancer.

In certain embodiments, the inactivated tumor cells or a mixture of different tumor cells are allogeneic tumor cells or autologous tumor cells or a mixture of the two.

The methods of the present invention may be directed to patients being treated for colorectal cancer, an aero-digestive squamous cancer, a lung cancer, a brain cancer, a liver cancer, a stomach cancer, a sarcoma, a leukemia, a lymphoma, a multiple myeloma, an ovarian cancer, a uterine cancer, a breast cancer, a melanoma, a prostate cancer, a pancreatic carcinoma, and a renal carcinoma.

DETAILED DESCRIPTION OF THE INVENTION

Figure 1:
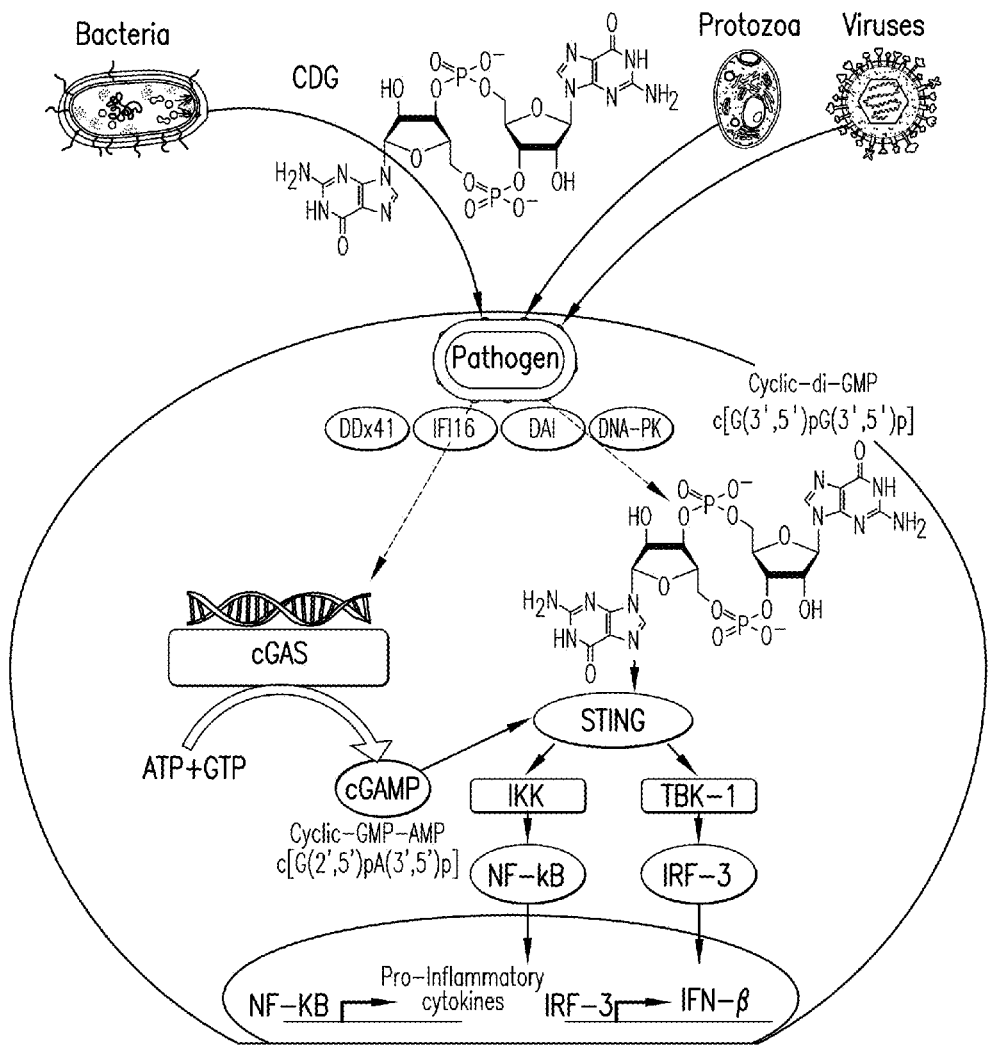
FIG. 1 depicts cyclic purine dinucleotide ("CDN")-mediated signaling. A CDN (e.g., c-di-AMP c-di-GMP, c-AMP-GMP), with the two purine nucleosides alternatively joined by a phosphate bridge with canonical bis-(3',5') linkages, or non-canonical 2',5' and 3',5' linkages, represented by c[G(2', 5')pA(3',5')p]. The canonical or non-canonical CDNs induce production of both NF-kB dependent pro-inflammatory cytokines, and also IFN-β by binding to the cytosolic receptor STING (Stimulator of Interferon Genes), activating signaling through the TBK-1/IRF-3 pathway, resulting in both autocrine and paracrine activation of DCs through binding to the IFN receptor and subsequent signaling.

The FDA approval of Provenge® (Dendreon Corporation) for the treatment of castration-resistant metastatic prostate cancer (mCRPC) has validated active cancer immunotherapy as a therapeutic area and reinvigorated the field. However, as an autologous dendritic cell (DC) based vaccine, Provenge® is impractical, complex and expensive, and provides only a modest—albeit significant—survival benefit. An improved cancer vaccine should be not only at least as effective as Provenge®, but also more practical, and preferably able to elicit objective responses. One step in this direction is ProstVac VF, a recombinant pox virus-based vaccine that encodes PSA and three co-stimulatory molecules (B7.1, ICAM-1, and Lfa-3). ProstVac VF was shown to increase overall survival in a randomized Phase 2 study conducted among men with mCRPC—though survival benefit did not reach p<0.05 statistical significance—and is currently being evaluated in a Phase 3 efficacy study. These vaccines use a single antigen expressed by both normal prostate tissue and prostate cancer. Targeting multiple cancer antigens with therapeutic vaccination strategies is desirable to reduce the potential negative impact of antigen-loss variants, patient-by-patient differences in tumor-associated antigen expression profiles, or MHC haplotype differences, all issues with single TAA vaccination strategies.

The present invention relates to a novel and highly active combination therapy which relies on a small molecule immune stimulator—cyclic-di-nucleotide (CDN)—that activates DCs via a recently discovered cytoplasmic receptor known as STING (Stimulator of Interferon Genes) formulated with irradiated allogeneic human tumor cell lines engineered to secrete high amounts of the DC growth factor, GM-CSF. This combination therapy can provide an ideal synergy of multiple tumor associated antigens, DC recruitment and proliferation (GM-CSF), coupled with a potent DC activation stimulus (CDN).

The CDNs cyclic-di-AMP (produced by *Listeria monocytogenes*) and its analog cyclic-di-GMP (produced by *Legionella pneumophila*) are recognized by the host cell as a PAMP (Pathogen Associated Molecular Pattern), which bind to the PRR (Pathogen Recognition Receptor) known as STING. STING is an adaptor protein in the cytoplasm of host mammalian cells which activates the TANK binding kinase (TBK1)-IRF3 signaling axis, resulting in the induction of IFN-β and other IRF-3 dependent gene products that strongly activate innate immunity. It is now recognized that STING is a component of the host cytosolic surveillance pathway, that senses infection with intracellular pathogens and in response induces the production of IFN-β, leading to the development of an adaptive protective pathogen-specific immune response consisting of both antigen-specific CD4 and CD8 T cells as well as pathogen-specific antibodies.

Definitions

"Administration" as it is used herein with regard to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell. By "administered together" it is not meant to be implied that two or more agents be administered as a single composition. Although administration as a single composition is contemplated by the present invention, such agents may be delivered to a single subject as separate administrations, which may be at the same or different time, and which may be by the same route or different routes of administration.

By "purified" and "isolated" is meant that a specified species accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the species present in a composition. The weights of water, buffers, salts, detergents, reductants, protease inhibitors, stabilizers (including an added protein such as albumin), and excipients are generally not used in the determination of purity.

"Specifically" or "selectively" binds, when referring to a ligand/receptor, nucleic acid/complementary nucleic acid, antibody/antigen, or other binding pair (e.g., a cytokine to a cytokine receptor) (each generally referred to herein as a "target biomolecule" or a "target") indicates a binding reaction which is related to the presence of the target in a heterogeneous population of proteins and other biologics. Specific binding can mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with a non-target molecule.

"Ligand" refers to a small molecule, nucleic acid, peptide, polypeptide, saccharide, polysaccharide, glycan, glycoprotein, glycolipid, or combinations thereof that binds to a target biomolecule. While such ligands may be agonists or antagonists of a receptor, a ligand also encompasses a binding agent that is not an agonist or antagonist, and has no agonist or antagonist properties. Specific binding of a ligand for its cognate target is often expressed in terms of an "Affinity." In preferred embodiments, the ligands of the present invention bind with affinities of between about $10^4$ $M^{-1}$ and about $10^8$ $M^{-1}$. Affinity is calculated as $K_d = k_{off}/k_{on}$ ($k_{off}$ is the dissociation rate constant, $K_{on}$ is the association rate constant and $K_d$ is the equilibrium constant).

Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988. In an alternative, affinity can be measured by isothermal titration calorimetry (ITC). In a typical ITC experiment, a solution of ligand is titrated into a solution of its cognate target. The heat released upon their interaction (ΔH) is monitored over time. As successive amounts of the ligand are titrated into the ITC cell, the quantity of heat absorbed or released is in direct proportion to the amount of binding. As the system reaches saturation, the heat signal diminishes until only heats of dilution are observed. A binding curve is then obtained from a plot of the heats from each injection against the ratio of ligand and binding partner in the cell. The binding curve is analyzed with the appropriate binding model to determine $K_B$, n and ΔH. Note that $K_B=1/K_d$.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a particular cancer which is being targeted by the compositions and methods of the present invention. Preferred cancers for treatment with the compositions described herein include, but are not limited to prostate cancer, renal carcinoma, melanoma, pancreatic cancer, cervical cancer, ovarian cancer, colon cancer, head & neck cancer, lung cancer and breast cancer.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: preventing a disease, improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: preventing a condition, improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Immunomodulatory Cell Lines

By "inactivated tumor cell" is meant a tumor cell (either "autologous" or "allogeneic" to the patient) which has which been treated to prevent division of the cells. For purposes of the present invention, such cells preserve their immunogenicity and their metabolic activity. Such tumor cells are genetically modified to express a transgene which is expressed within a patient as part of cancer therapy. Thus, a composition or vaccine of the invention comprises neoplastic (e.g., tumor) cells that are autologous or allogeneic to the patient undergoing treatment and is most preferably the same general type of tumor cell as is afflicting the patient. For example, a patient suffering from melanoma will typically be administered a genetically modified cell derived from a melanoma. Methods for inactivating tumor cells for use in the present invention, such as the use of irradiation, are well known in the art.

The inactivated tumor cells of the present invention are administered to the patient together with one or more costimulatory molecules or agents. A preferred costimulatory agent comprises one or more cytokines which stimulate dendritic cell induction, recruitment, and/or maturation. Methods for assessing such costimulatory agents are well known in the literature. Induction and maturation of DCs is typically assessed by increased expression of certain membrane molecules such as CD80 and CD86, and/or secretion of pro-inflammatory cytokines, such as IL-12 and type I interferons following stimulation.

In preferred embodiments, the inactivated tumor cells themselves are modified to express and secrete one or more cytokines which stimulate dendritic cell induction, recruitment, and/or maturation. The present invention is described in exemplary terms with regard to the use of GM-CSF. Thus, by way of example, the tumor cell may express a transgene encoding GM-CSF as described in U.S. Pat. Nos. 5,637,483, 5,904,920, 6,277,368 and 6,350,445, as well as in US Patent Publication No. 20100150946, each of which is expressly incorporated by reference herein. A form of GM-CSF-expressing genetically modified cancer cells or a "cytokine-expressing cellular vaccine" for the treatment of pancreatic cancer is described in U.S. Pat. Nos. 6,033,674 and 5,985, 290, both of which are expressly incorporated by reference herein.

Other suitable cytokines which may be expressed by such inactivated tumor cells and/or bystander cells instead of, or together with, GM-CSF include, but are not limited to, one or more of CD40 ligand, IL-12, CCL3, CCL20, and CCL21. This list is not meant to be limiting.

While it is preferred that the inactivated tumor cells administered to the subject express one or more cytokines of interest, the tumor cell line may be accompanied by an inactivated bystander cell line which expresses and secretes one or more cytokines which stimulate dendritic cell induction, recruitment, and/or maturation. The bystander cell line may provide all of the cytokines which stimulate dendritic cell induction, recruitment, and/or maturation, or may supplement cytokines which stimulate dendritic cell induction, recruitment, and/or maturation expressed and secreted by the inactivated tumor cells. By way of example, immunomodulatory cytokine-expressing bystander cell lines are disclosed in U.S. Pat. Nos. 6,464,973, and 8,012,469, Dessureault et al., Ann. Surg. Oncol. 14: 869-84, 2007, and Eager and Nemunaitis, Mol. Ther. 12: 18-27, 2005, each of which is expressly incorporated by reference herein.

By "Granulocyte-macrophage colony stimulating factor (GM-CSF) polypeptide" is meant a cytokine or fragment thereof having immunomodulatory activity and having at least about 85% amino acid sequence identity to GenBank Accession No. AAA52122.1.

Cyclic Purine Dinucleotides

As described herein, another of these costimulatory agents is a cyclic purine dinucleotide which binds to STING and induces STING-dependent TBK1 activation. Other costimulatory molecules which may be included are described hereinafter.

Prokaryotic as well as eukaryotic cells use various small molecules for cell signaling and intra- and intercellular communication. Cyclic nucleotides like cGMP, cAMP, etc. are known to have regulatory and initiating activity in pro- and eukaryotic cells. Unlike eukaryotic cells, prokaryotic cells also use cyclic purine dinucleotides as regulatory molecules. In prokaryotes, the condensation of two GTP molecules is catalyst by the enzyme diguanylate cyclase (DGC) to give c-diGMP, which represents an important regulator in bacteria.

Recent work suggests that cyclic diGMP or analogs thereof can also stimulate or enhance immune or inflammatory response in a patient or can enhance the immune response to a vaccine by serving as an adjuvant in mammals. Cytosolic detection of pathogen-derived DNA requires signaling through TANK binding kinase 1 (TBK1) and its downstream transcription factor, IFN-regulatory factor 3 (IRF3). A transmembrane protein called STING (stimulator of IFN genes; also known as MITA, ERIS, MPYS and TMEM173) functions as the signaling receptor for these cyclic purine dinucleotides, causing stimulation of the TBK1-IRF3 signalling axis and a STING-dependent type I interferon response. See, e.g., FIG. 1. Burdette et al., Nature 478: 515-18, 2011 demonstrated that STING binds directly to cyclic diguanylate monophosphate, but not to other unrelated nucleotides or nucleic acids.

Suitable cyclic purine dinucleotides for use in the present invention are described in some detail in, e.g., U.S. Pat. Nos. 7,709,458 and 7,592,326; WO2007/054279; and Yan et al., Bioorg. Med. Chem. Lett. 18: 5631 (2008), each of which is hereby incorporated by reference. Preferred cyclic purine dinucleotides include, but are not limited to, c-di-AMP, c-di-GMP, c-di-IMP, c-AMP-GMP, c-AMP-IMP, and c-GMP-IMP, and analogs thereof including, but not limited to, phosphorothioate analogues.

Adjuvants

In addition to the inactivated tumor cell(s) and cyclic purine dinucleotide(s) described above, the compositions of the present invention may further comprise one or more additional substances which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-1-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profilin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacterial. α-Galactosylceramide (α-GalCer) is an activator of natural killer T (NKT) cells. Muramyl dipeptide is a bioactive peptidoglycan motif common to all bacteria. This list is not meant to be limiting. Preferred adjuvant compositions are described below.

CTLA-4 and PD-1 Pathway Antagonists

CTLA-4 is thought to be an important negative regulator of the adaptive immune response. Activated T cells upregulate CTLA-4, which binds CD80 and CD86 on antigen-presenting cells with higher affinity than CD28, thus inhibiting T-cell stimulation, IL-2 gene expression and T-cell proliferation. Anti-tumor effects of CTLA4 blockade have been observed in murine models of colon carcinoma, metastatic prostate cancer, and metastatic melanoma.

Ipilimumab (Yervoy™) and tremelimumab are humanized monoclonal antibodies that bind to human CTLA4 and prevent its interaction with CD80 and CD86. Phase I and II studies using ipilimumab and tremelimumab have demonstrated clinical activity in cancer patients. Other negative immune regulators which may be targeted by a similar strategy include programmed cell death 1, B and T lymphocyte attenuator, transforming growth factor beta β, interleukin-10, and vascular endothelial growth factor.

PD-1 is another negative regulator of adaptive immune response that is expressed on activated T-cells. PD-1 binds to B7-H1 and B7-DC, and the engagement of PD-1 suppresses T-cell activation. Anti-tumor effects have been demonstrated with PD-1 pathway blockade. BMS-936558, MK3475, CT-011, AMP-224 and MDX-1106 have been reported in the literature to be examples of PD-1 pathway blockers which may find use in the present invention.

TLR Agonists

The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-1R) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity.

In humans, ten TLR have been identified. TLRs that are expressed on the surface of cells include TLR-1, -2, -4, -5, and -6, while TLR-3, -7/8, and -9 are expressed with the ER compartment. Human dendritic cell subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following:

Pam3Cys, a TLR-1/2 agonist;
CFA, a TLR-2 agonist;
MALP2, a TLR-2 agonist;
Pam2Cys, a TLR-2 agonist;
FSL-1, a TLR-2 agonist;
Hib-OMPC, a TLR-2 agonist;

polyribosinic:polyribocytidic acid (Poly I:C), a TLR-3 agonist;
polyadenosine-polyuridylic acid (poly AU), a TLR-3 agonist;
Polyinosinic-Polycytidylic acid stabilized with poly-L-lysine and carboxymethylcellulose (Hiltonol®), a TLR-3 agonist;
monophosphoryl lipid A (MPL), a TLR-4 agonist;
LPS, a TLR-4 agonist;
bacterial flagellin, a TLR-5 agonist;
sialyl-Tn (STn), a carbohydrate associated with the MUC1 mucin on a number of human cancer cells and a TLR-4 agonist;
imiquimod, a TLR-7 agonist;
resiquimod, a TLR-7/8 agonist;
loxoribine, a TLR-7/8 agonist; and
unmethylated CpG dinucleotide (CpG-ODN), a TLR-9 agonist.

Because of their adjuvant qualities, TLR agonists are preferably used in combinations with other vaccines, adjuvants and/or immune modulators, and may be combined in various combinations. Thus, in certain embodiments, the cyclic purine dinucleotides that bind to STING and induces STING-dependent TBK1 activation and an inactivated tumor cell which expresses and secretes one or more cytokines which stimulate dendritic cell induction, recruitment and/or maturation, as described herein can be administered together with one or more TLR agonists for therapeutic purposes.

Lipids and Liposomes

Liposomes are vesicles formed from one ("unilamellar") or more ("multilamellar") layers of phospholipid. Because of the amphipathic character of the phospholipid building blocks, liposomes typically comprise a hydrophilic layer presenting a hydrophilic external face and enclosing a hydrophilic core. The versatility of liposomes in the incorporation of hydrophilic/hydrophobic components, their non-toxic nature, biodegradability, biocompatibility, adjuvanticity, induction of cellular immunity, property of sustained release and prompt uptake by macrophages, makes them attractive candidates for the delivery of antigens.

WO2010/104833, which is incorporated by reference herein in its entirety, describes liposomal preparations which comprise:
a) an aqueous vehicle;
b) liposomes comprising
(i) dimyristoylphosphatidylcholine ("DMPC"),
(ii) dimyristoylphosphatidylglycerol ("DMPG"), dimyristoyltrimethylammonium propane ("DMTAP"), or both DMPG and DMTAP, and
(iii) at least one sterol derivative; and
c) one or more immunogenic polypeptide(s) or carbohydrate(s) covalently linked to between 1% and 100% of said at least one sterol derivative.

Such liposomal formulations, referred to herein as VesiVax® (Molecular Express, Inc.), with our without the "immunogenic polypeptide(s) or carbohydrate(s)" referred to above, can contain one or more additional components such as peptidoglycan, lipopeptide, lipopolysaccharide, monophosphoryl lipid A, lipoteichoic acid, resiquimod, imiquimod, flagellin, oligonucleotides containing unmethylated CpG motifs, beta-galactosylceramide, muramyl dipeptide, all-trans retinoic acid, double-stranded viral RNA, heat shock proteins, dioctadecyldimethylammonium bromide, cationic surfactants, toll-like receptor agonists, dimyristoyltrimethylammoniumpropane, and nod-like receptor agonists. Advantageously, these liposomal formulations can be used to deliver one or more cyclic purine dinucleotides in accordance with the present invention.

Moreover, while the liposomal formulations discussed above employ a "steroid derivative" as an anchor for attaching an immunogenic polypeptide or carbohydrate to a liposome, the steroid may simply be provided as an unconjugated steroid such as cholesterol.

Suitable methods for preparing liposomes from lipid mixtures are well known in the art. See, e.g., Basu & Basu, *Liposome Methods and Protocols* (*Methods in Molecular Biology*), Humana Press, 2002; Gregoriadis, *Liposome Technology*, 3$^{rd}$ *Edition*, Informa HealthCare, 2006. Preferred methods include extrusion, homogenization, and sonication methods described therein. An exemplary method for preparing liposomes for use in the present invention, which comprises drying a lipid mixture, followed by hydration in an aqueous vehicle and sonication to form liposomes, is described in WO2010/104833.

In certain embodiments, the liposomes are provided within a particular average size range. Liposome size can be selected, for example, by extrusion of an aqueous vehicle comprising liposomes through membranes having a preselected pore size and collecting the material flowing through the membrane. In preferred embodiments, the liposomes are selected to be substantially between 50 and 500 nm in diameter, more preferably substantially between 50 and 200 nm in diameter, and most preferably substantially between 50 and 150 nm in diameter. The term "substantially" as used herein in this context means that at least 75%, more preferably 80%, and most preferably at least 90% of the liposomes are within the designated range.

Other lipid and lipid-like adjuvants which may find use in the present invention include oil-in-water (o/w) emulsions (see, e.g., Muderhwa et al., J. Pharmaceut. Sci. 88: 1332-9, 1999)), VesiVax® TLR (Molecular Express, Inc.), digitonin (see, e.g., U.S. Pat. No. 5,698,432), and glucopyranosyl lipids (see, e.g., United States Patent Application 20100310602).

Chemotherapeutic Agents

In additional embodiments the methods further involve administering to the subject an effective amount of one or more chemotherapeutics as an additional treatment for the patient's tumor. In certain embodiments the one or more chemo therapeutics is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

Pharmaceutical Compositions

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in Remington, The Science and Practice of Pharmacy 21$^{st}$ Edition (Mack Publishing Co., Easton, Pa.) and Nielloud and Marti-Mestres, Pharmaceutical Emulsions and Suspensions: 2$^{nd}$ Edition (Marcel Dekker, Inc, New York).

For the purposes of this disclosure, the pharmaceutical compositions may be administered by a variety of means including orally, parenterally, by inhalation spray, topically, or rectally in formulations containing pharmaceutically acceptable carriers, adjuvants and vehicles. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made in a suitable machine using a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

As used herein, pharmaceutically acceptable salts include, but are not limited to: acetate, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of pharmaceutical composition. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

As noted, the compositions of the present invention are preferably formulated as pharmaceutical compositions for parenteral or enteral delivery. A typical pharmaceutical composition for administration to an animal comprises a pharmaceutically acceptable vehicle such as aqueous solutions, non-toxic excipients, including salts, preservatives, buffers and the like. See, e.g., *Remington's Pharmaceutical Sciences*, 15*th Ed*., Easton ed., Mack Publishing Co., pp 1405-1412 and 1461-1487 (1975); *The National Formulary XIV,* 14*th Ed*., American Pharmaceutical Association, Washington, D.C. (1975). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to routine skills in the art.

Repeated administrations of a particular vaccine (homologous boosting) have proven effective for boosting humoral responses. Such an approach may not be effective at boosting cellular immunity because prior immunity to the vector tends to impair robust antigen presentation and the generation of appropriate inflammatory signals. One approach to circumvent this problem has been the sequential administration of vaccines that use different antigen-delivery systems (heterologous boosting). In a heterologous boosting regimen, at least one prime or boost delivery comprises delivery of the inactivated tumor cell/cyclic purine dinucleotide compositions described herein. The heterologous arm of the regimen may comprise delivery of antigen using one or more of the following strategies:

inactivated bacteria or viruses comprising the antigen of interest, which are particles that have been treated with some denaturing condition to render them ineffective or inefficient in mounting a pathogenic invasion;

purified antigens, which are typically naturally-produced antigens purified from a cell culture of the pathogen or a tissue sample containing the pathogen, or a recombinant version thereof;

live viral or bacterial delivery vectors recombinantly engineered to express and/or secrete antigens in the host cells of the subject. These strategies rely on attenuating (e.g., via genetic engineering) the viral or bacterial vectors to be non-pathogenic and non-toxic;

antigen presenting cell (APC) vectors, such as a dendritic cell (DC) vector, which comprise cells that are loaded with an antigen, or transfected with a composition comprising a nucleic acid encoding the antigen (e.g., Provenge® (Dendreon Corporation) for the treatment of castration-resistant metastatic prostate cancer);

liposomal antigen delivery vehicles; and naked DNA vectors and naked RNA vectors which may be administered by a gene gun, electroporation, bacterial ghosts, microspheres, microparticles, liposomes, polycationic nanoparticles, and the like.

A prime vaccine and a boost vaccine can be administered by any one or combination of the following routes. In one aspect, the prime vaccine and boost vaccine are administered by the same route. In another aspect, the prime vaccine and boost vaccine are administered by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, intratumor, peritumor, intratumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

REFERENCES

1. Kantoff P W, Higano C S, Shore N D, et al. Sipuleucel-T immunotherapy for castration-resistant prostate cancer. The New England journal of medicine 2010; 363:411-22.
2. Dranoff G, Jaffee E, Lazenby A, et al. Vaccination with irradiated tumor cells engineered to secrete murine granulocyte-macrophage colony-stimulating factor stimulates potent, specific, and long-lasting anti-tumor immunity. Proceedings of the National Academy of Sciences of the United States of America 1993; 90:3539-43.
3. Mellman I, Coukos G, Dranoff G. Cancer immunotherapy comes of age. Nature 2011; 480:480-9.
4. Lutz E, Yeo C J, Lillemoe K D, et al. A lethally irradiated allogeneic granulocyte-macrophage colony stimulating factor-secreting tumor vaccine for pancreatic adenocarcinoma. A Phase II trial of safety, efficacy, and immune activation. Annals of surgery 2011; 253:328-35.
5. Le D T, Pardoll D M, Jaffee E M. Cellular vaccine approaches. Cancer J 2010; 16:304-10.
6. Witte C E, Archer K A, Rae C S, Sauer J D, Woodward J J, Portnoy D A. Innate immune pathways triggered by *Listeria monocytogenes* and their role in the induction of cell-mediated immunity. Advances in immunology 2012; 113:135-56.

7. Woodward J J, Iavarone A T, Portnoy D A. c-di-AMP secreted by intracellular *Listeria monocytogenes* activates a host type I interferon response. Science 2010; 328:1703-5.
8. Burdette D L, Monroe K M, Sotelo-Troha K, et al. STING is a direct innate immune sensor of cyclic di-GMP. Nature 2011; 478:515-8.
9. Jemal A, Siegel R, Xu J, Ward E. Cancer statistics, 2010. CA: a cancer journal for clinicians 2010; 60:277-300.
10. Di Lorenzo G, Buonerba C, Kantoff P W. Immunotherapy for the treatment of prostate cancer. Nature reviews Clinical oncology 2011; 8:551-61.
11. Topalian S L, Weiner G J, Pardoll D M. Cancer Immunotherapy Comes of Age. Journal of clinical oncology: official journal of the American Society of Clinical Oncology 2011.
12. Blankenstein T, Coulie P G, Gilboa E, Jaffee E M. The determinants of tumour immunogenicity. Nature reviews Cancer 2012.
13. Pardoll D. The blockade of immune checkpoints in cancer immunotherapy. Nature reviews Cancer 2012; 12:253-64.
14. Gulley J L, Arlen P M, Madan R A, et al. Immunologic and prognostic factors associated with overall survival employing a poxyiral-based PSA vaccine in metastatic castrate-resistant prostate cancer. Cancer immunology, immunotherapy: CII 2010; 59:663-74.
15. Kantoff P W, Schuetz T J, Blumenstein B A, et al. Overall survival analysis of a phase II randomized controlled trial of a Poxyiral-based PSA-targeted immunotherapy in metastatic castration-resistant prostate cancer. Journal of clinical oncology: official journal of the American Society of Clinical Oncology 2010; 28:1099-105.
16. Barber G N. STING-dependent signaling. Nature immunology 2011; 12:929-30.
17. Ishikawa H, Barber G N. The STING pathway and regulation of innate immune signaling in response to DNA pathogens. Cellular and molecular life sciences: CMLS 2011; 68:1157-65.
18. Crimmins G T, Herskovits A A, Rehder K, et al. *Listeria monocytogenes* multidrug resistance transporters activate a cytosolic surveillance pathway of innate immunity. Proceedings of the National Academy of Sciences of the United States of America 2008.
19. Leber J H, Crimmins G T, Raghavan S, Meyer-Morse N P, Cox J S, Portnoy D A. Distinct TLR- and NLR-mediated transcriptional responses to an intracellular pathogen. PLoS Pathog 2008; 4:e6.
20. O'Riordan M, Yi C H, Gonzales R, Lee K D, Portnoy D A. Innate recognition of bacteria by a macrophage cytosolic surveillance pathway. Proceedings of the National Academy of Sciences of the United States of America 2002; 99:13861-6.
21. Sun J C, Bevan M J. Defective CD8 T cell memory following acute infection without CD4 T cell help. Science 2003; 300:339-42.
22. Bahjat K S, Liu W, Lemmens E E, et al. Activation of a Cytosolic Surveillance Pathway Controls CD8+ T Cell Potency During Bacterial Infection. In; 2005.
23. Bahjat K S, Liu W, Lemmens E E, et al. Cytosolic Entry Controls CD8+-T-Cell Potency during Bacterial Infection. Infection and immunity 2006; 74:6387-97.
24. Reed S G, Bertholet S, Coler R N, Friede M. New horizons in adjuvants for vaccine development. Trends in immunology 2009; 30:23-32.
25. Dubensky T W, Jr., Reed S G. Adjuvants for cancer vaccines. Seminars in immunology 2010; 22:155-61.
26. Ahmed S S, Plotkin S A, Black S, Coffman R L. Assessing the safety of adjuvanted vaccines. Science translational medicine 2011; 3:93rv2.
27. Olson K, Macias P, Hutton S, Ernst W A, Fujii G, Adler-Moore J P. Liposomal gD ectodomain (gD1-306) vaccine protects against HSV2 genital or rectal infection of female and male mice. Vaccine 2009; 28:548-60.
28. Adler-Moore J, Munoz M, Kim H, et al. Characterization of the murine Th2 response to immunization with liposomal M2e influenza vaccine. Vaccine 2011; 29:4460-8.
29. Drake C G, Doody A D, Mihalyo M A, et al. Androgen ablation mitigates tolerance to a prostate/prostate cancer-restricted antigen. Cancer cell 2005; 7:239-49.
30. Antonarakis E S, Drake C G. Combining immunological and androgen-directed approaches: an emerging concept in prostate cancer immunotherapy. Current opinion in oncology 2012.
31. Brahmer J R, Drake C G, Wollner I, et al. Phase I study of single-agent anti-programmed death-1 (MDX-1106) in refractory solid tumors: safety, clinical activity, pharmacodynamics, and immunologic correlates. Journal of clinical oncology: official journal of the American Society of Clinical Oncology 2010; 28:3167-75.
32. Hodi F S, O'Day S J, McDermott D F, et al. Improved survival with ipilimumab in patients with metastatic melanoma. The New England journal of medicine 2010; 363:711-23.
33. Pardoll D, Drake C. Immunotherapy earns its spot in the ranks of cancer therapy. The Journal of experimental medicine 2012; 209:201-9.
34. Tannock I F, de Wit R, Berry W R, et al. Docetaxel plus prednisone or mitoxantrone plus prednisone for advanced prostate cancer. The New England journal of medicine 2004; 351:1502-12.
35. Kastenmuller K, Wille-Reece U, Lindsay R W, et al. Protective T cell immunity in mice following protein-TLR7/8 agonist-conjugate immunization requires aggregation, type I IFN, and multiple DC subsets. The Journal of clinical investigation 2011; 121:1782-96.
36. Coffman R L, Sher A, Seder R A. Vaccine adjuvants: putting innate immunity to work. Immunity 2010; 33:492-503.
37. Kasturi S P, Skountzou I, Albrecht R A, et al. Programming the magnitude and persistence of antibody responses with innate immunity. Nature 2011; 470:543-7.
38. Einstein M H, Baron M, Levin M J, et al. Comparison of the immunogenicity and safety of Cervarix and Gardasil human papillomavirus (HPV) cervical cancer vaccines in healthy women aged 18-45 years. Human vaccines 2009; 5:705-19.
39. van Elsas A, Sutmuller R P M, Hurwitz A A, et al. Elucidating the Autoimmune and Antitumor Effector Mechnaisms of a Treatment Based on Cytotoxic T Lymphocyte Antigen-4 Blockade in Combination with a B16 Melanoma Vaccine: Comparison of Prophylaxis and Therapy. J Exp Med 2001; 194:481-9.
40. Curran M A, Allison J P. Tumor vaccines expressing flt3 ligand synergize with ctla-4 blockade to reject preimplanted tumors. Cancer research 2009; 69:7747-55.
41. Waitz R, Solomon S B, Petre E N, et al. Potent induction of tumor immunity by combining tumor cryoablation with anti-CTLA-4 therapy. Cancer research 2012; 72:430-9.
42. Fasso M, Waitz R, Hou Y, et al. SPAS-1 (stimulator of prostatic adenocarcinoma-specific T cells)/SH3GLB2: A prostate tumor antigen identified by CTLA-4 blockade. Proceedings of the National Academy of Sciences of the United States of America 2008; 105:3509-14.

43. Hurwitz A A, Foster B A, Allison J P, Greenberg N M, Kwon E D. The TRAMP mouse as a model for prostate cancer. Current protocols in immunology/edited by John E Coligan [et al] 2001; Chapter 20: Unit 20 5.
44. Hernandez J M, Bui M H, Han K R, et al. Novel kidney cancer immunotherapy based on the granulocyte-macrophage colony-stimulating factor and carbonic anhydrase IX fusion gene. Clinical cancer research: an official journal of the American Association for Cancer Research 2003; 9:1906-16.
45. Goldberg M V, Maris C H, Hipkiss E L, et al. Role of PD-1 and its ligand, B7-H1, in early fate decisions of CD8 T cells. Blood 2007; 110:186-92.
46. Le D T, Brockstedt D G, Nir-Paz R, et al. A live-attenuated Listeria vaccine (ANZ-100) and a live-attenuated Listeria vaccine expressing mesothelin (CRS-207) for advanced cancers: phase i studies of safety and immune induction. Clinical cancer research: an official journal of the American Association for Cancer Research 2012; 18:858-68.
47. Brockstedt D G, Giedlin M A, Leong M L, et al. Listeria-based cancer vaccines that segregate immunogenicity from toxicity. Proceedings of the National Academy of Sciences of the United States of America 2004; 101:13832-7.
48. Bahjat K S, Prell R A, Allen H E, et al. Activation of immature hepatic NK cells as immunotherapy for liver metastatic disease. J Immunol 2007; 179:7376-84.

EXAMPLES

The following examples serve to illustrate the present invention. These examples are in no way intended to limit the scope of the invention.

Example 1

One approach to stimulate immunity against a broad repertoire of TAAs is "GVAX," which are vaccines based on allogeneic human tumor cell lines that are engineered to secrete GM-CSF, the primary cytokine that stimulates DC recruitment, differentiation and maturation. GVAX vaccines have formed the basis of multiple clinical trials in several cancer indications, and have been shown to be safe, well-tolerated, immunogenic and shown to provide some clinical benefit. A Phase 3 clinical study comparing prostate GVAX immunotherapy (G) to docetaxel plus prednisone (D+P) in men with mCRPC was prematurely terminated by the sponsor when an early unscheduled futility analysis revealed that the trial had <30% chance of meeting its predefined primary endpoint of improvement in overall survival. Continued follow-up and analysis of the >600 patients on study, however, revealed that the Kaplan-Meier survival curve for the G arm crossed above the D+P arm at ~21 months. Furthermore, patients with a predicted survival time of ≥18 months at baseline, based on the Halabi nomogram, had a 2.5 month survival benefit when treated with GVAX, with a 30% "tail" of long-term survivors, as compared to chemotherapy These results showed that GVAX prostate immunotherapy provided a survival benefit over chemotherapy, which correspondingly shows ~2 month survival benefit as compared to placebo.

Since TLR-targeted adjuvants used individually that signal through MyD88- and TRIF-dependent pathways are typically poor inducers of CD8 T cell immunity, we assessed whether CDN, which signals through the cytoplasmic STING receptor, could facilitate priming of both MHC class I- and class II-restricted immunity. CDN induced priming of both Th1 CD4 and CD8 T cells specific for the vaccine recombinant protein Ag, HIV Gag or OVA. Balb/c mice were vaccinated twice subcutaneously in the base of the tail (s.c.) 3 wks apart with 5 µg of HIV Gag protein formulated with 2% oil-in-water adjuvant (Addavax, Invivogen) and CDN at the dose level indicated in FIG. 2.

Figure 2A:
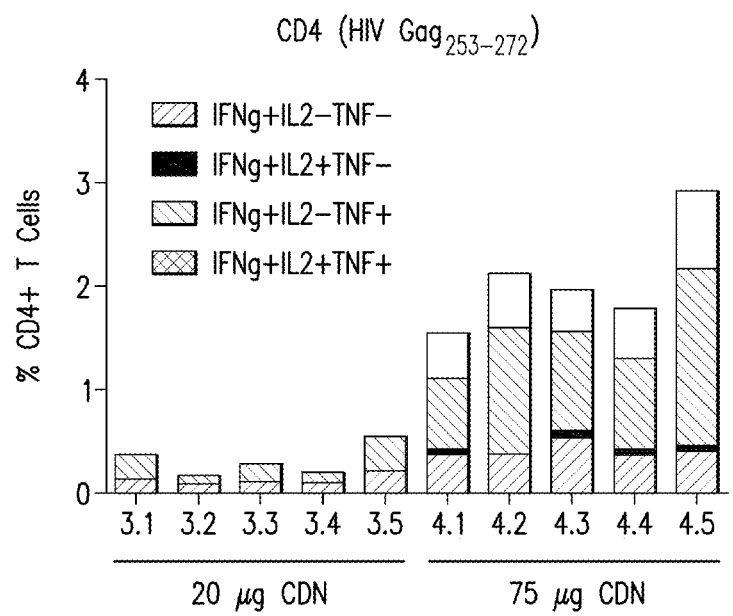
FIG. 2A depicts CDN-adjuvinated T-cell responsiveness to HIV Gag.

As shown in FIG. 2A, CDN-adjuvanted HIV Gag vaccines induce a polyfunctional Ag-specific Th1 CD4 T cell response. The secondary CD4 T cell response was measured at 5 days post boost by intracellular cytokine staining of IFN-γ, IL-2 and TNF-α positive splenocytes following stimulation with the I-A$^d$ restricted HIV Gag epitope. Bars represent individual mice. As shown in FIG. 4B, the magnitude of the CDN-dependent vaccine induced T cell response is enhanced by formulation of CDN with VesiVax® liposomes.

Figure 2B:
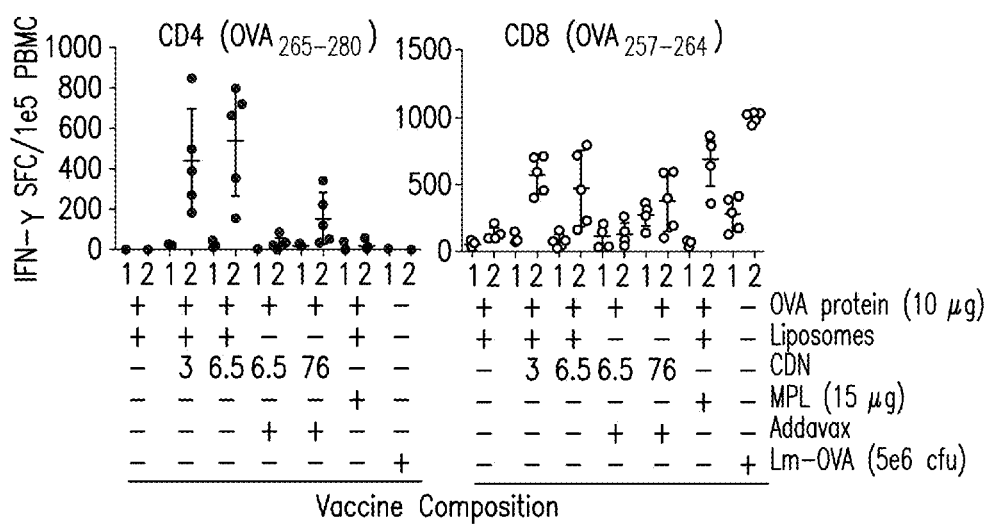
FIG. 2B depicts The primary and secondary OVA-specific CD4 and CD8 T cell response in PBMC following immunization of mice with the vaccine compositions shown in the figure.
Figure 2C:
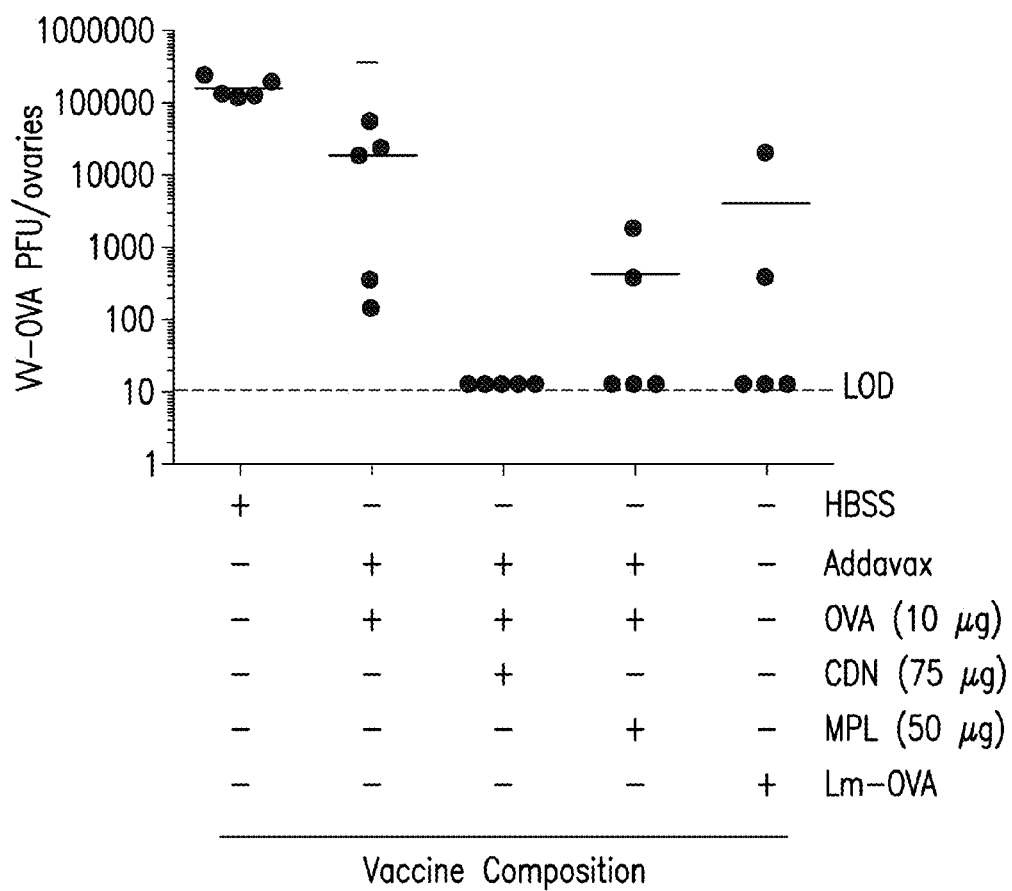
FIG. 2C depicts immune responses induced by CDN-adjuvanted vaccines using OVA as a model antigen.

The primary (1) and secondary (2) OVA-specific CD4 and CD8 T cell response in PBMC following s.c. immunization of groups of 5 C57BL/6 mice with the vaccine compositions shown in FIG. 2 was measured by IFN-γ ELISPOT, and the results depicted in FIG. 2C. Groups of 5 C57BL/6 mice were immunized s.c. twice at a 3-wk interval with the vaccines indicated in the Figure, or with $5\times10^6$ CFU of Lm-OVA, given i.v. At 4 weeks post boost, mice were challenged with $5\times10^5$ PFU of VV-OVA, and 5 days later the ovaries were harvested, processed and VV-OVA was quantitated by plaque assay.

As shown in the figure, vaccine potency was dependent on formulation, and our initial results indicate that formulation with VesiVax® liposomes was optimal, due likely to efficient vaccine delivery into the cytosol. Notably, mice vaccinated with CDN-adjuvanted OVA were completely protected by challenge with vaccinia virus. By comparison with the negative control group given HBSS, this level of protection was >4 logs. The level of protection afforded by the CDN-adjuvanted vaccine was better than either MPL-adjuvanted OVA (using the human MPL dose of 50 µg), or Listeria-OVA vaccines.

Figure 7:
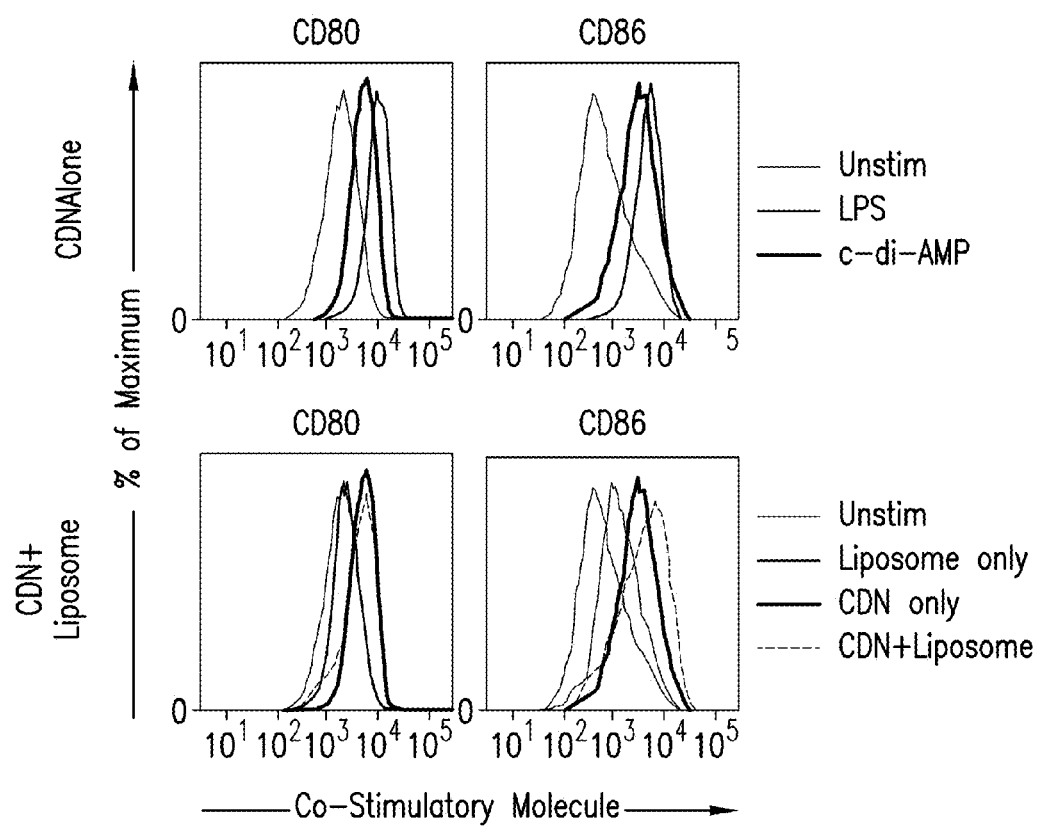
FIG. 7 depicts the induction of human dendritic cells upon CDN treatment, as assessed by expression of costimulatory molecules.

FIG. 7 depicts the induction of human dendritic cells upon CDN treatment, as assessed by expression of costimulatory molecules such as CD80 and CD86. In this experiment, CD14+ monocytes were isolated from PBMC and cultured in the presence of GM-CSF and IL-4. On day 6, $10^5$ DCs were treated with 100 ng/ML LPS, 20 µM CDN (c-di-AMP); 369 µg liposomes (VesiVax®), or liposomes plus CDN, as indicated in the figure. The indicated costimulatory molecules were detected 48 hrs later by flow cytometry. As noted, liposomes substantially improve the ability of CDN to induce dendritic cell maturation.

Example 2

The B16 melanoma tumor model is aggressive and poorly immunogenic, and therapeutic vaccination with irradiated GM-CSF secreting B16 melanoma tumor cells (B16-GM) has not been effective unless combined with blockade of immune checkpoints, such as CTLA-4 or PD-1. In this example, we show that a single injection of STINGVAX (CDN formulated with digitonin and incubated with irradiated B16-GM) significantly inhibited the growth of established palpable B16 tumors, when administered at 7 days post B16 tumor cell implantation when the tumor was palpable and established.

Figure 3A:
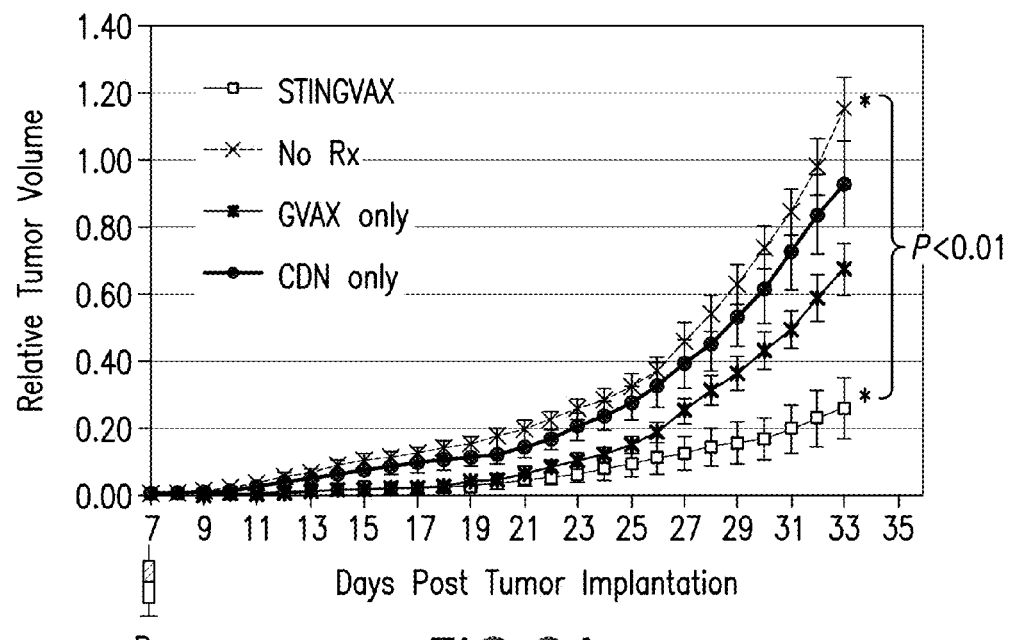
FIG. 3A depicts growth inhibition of B16 melanoma in response to a GVAX/CDN combination vaccine (referred to as "Stingvax").

$5\times10^4$ B16 melanoma cells were inoculated in the footpad of C57BL/6 mice and when tumors were palpable at 7 days, mice were injected once s.c. in the contralateral thigh with the vaccines indicated in FIG. 3. The following amounts of vaccine components were used for each injection: irradiated B16 GM-CSF (GVAX), 1.5×10$^6$ cells; CDN only, 20 ng; digitonin, 10 µg/mL. STINGVAX was prepared by incubation of irradiated B16 GM-CSF with CDN and digitonin at 20° C. for 30 min, washing 3× with PBS, and the resulting composition injected after resuspension in 200 µL of PBS. See also Woodward et al., Supporting online material 27 May 2010 on Science Express DOI: 10.1126/science. 1189801, for formulation information. Tumor growth was measured daily. Growth was significantly inhibited by STINGVAX vs No Rx Group (P<0.01). As shown in FIG. 3A, tumor inhibition was dependent on combination of B16-GM with CDN, as treatment with either component alone had no impact on tumor growth as compared to untreated control mice. Additionally, the CD8 T cell response specific for p15E, an endogenous retrovirus-specific Ag expressed on the B16 tumor, was enhanced in STINGVAX-treated tumor-bearing mice, compared to B16-GM treated mice (data not shown).

Figure 3B:
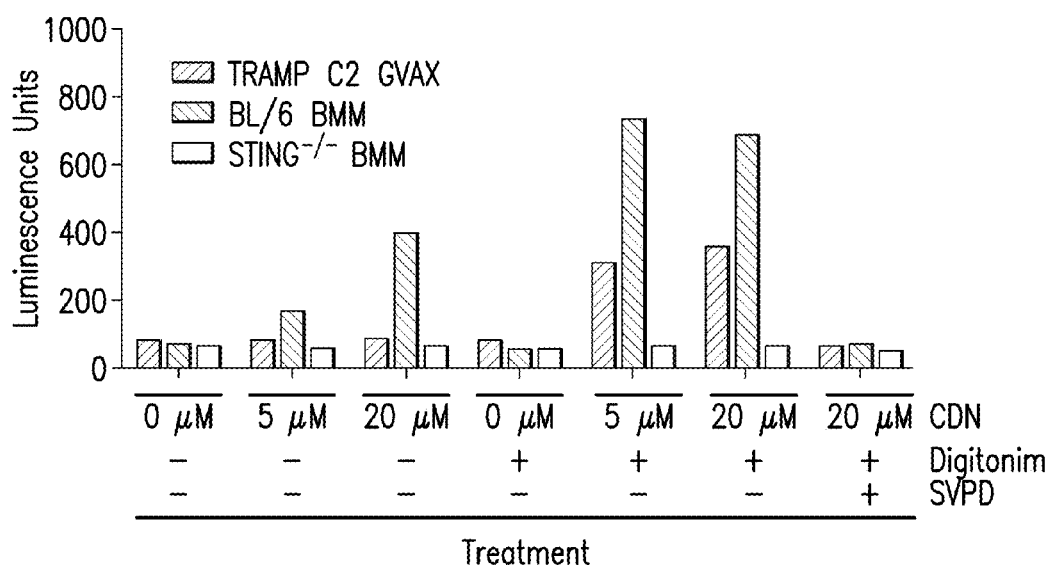
FIG. 3B depicts interferon-β induction in TRAMP-GM cells and bone marrow-derived macrophages in response to a GVAX/CDN combination vaccine.

From these data, it is believed that the synergy between STING-targeted CDN and irradiated GM-secreting tumor cell vaccines requires that the CDN-dependent induction of IFN-β results in the activation of GM-CSF-differentiated DCs, thus providing a strong "Signal 3," resulting in a more-effective antitumor T cell response. For this reason, we determined whether CDN could directly induce the production of IFN-β in TRAMP-GM cells. As shown in FIG. 3B, when formulated with digitonin, CDN efficiently induced the expression of IFN-β in both TRAMP-GM and primary macrophages, but not in macrophages from goldenticket (gt) mice which lack a functional STING protein.

Figure 4:
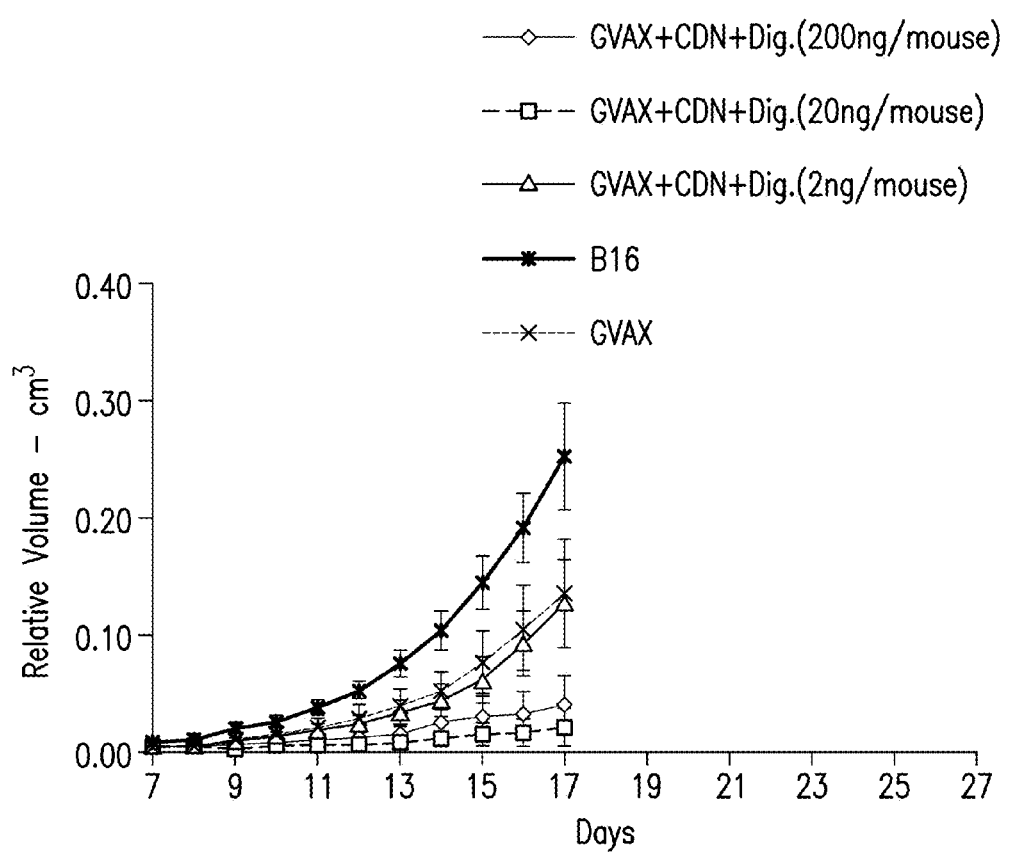
FIG. 4 depicts concentration dependence of growth inhibition of B16 melanoma in response to a GVAX/CDN combination vaccine.
Figure 5A:
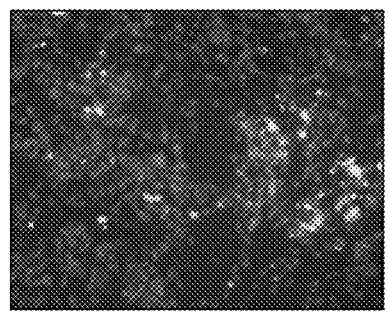
FIG. 5A depicts CD8+ T-cell infiltration of untreated B16 melanoma tumors.
Figure 5B:
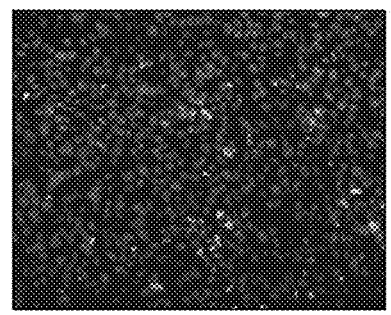
FIG. 5B depicts CD8+ T-cell infiltration of B16 melanoma tumors in cells treated with CDN.
Figure 5C:
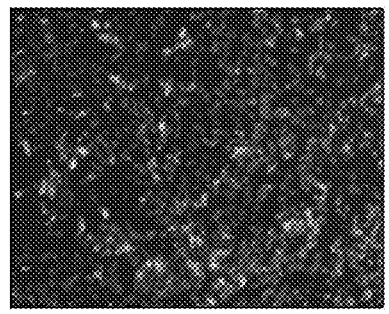
FIG. 5C depicts CD8+ T-cell infiltration of B16 melanoma tumors in cells treated with GVAX.
Figure 5D:
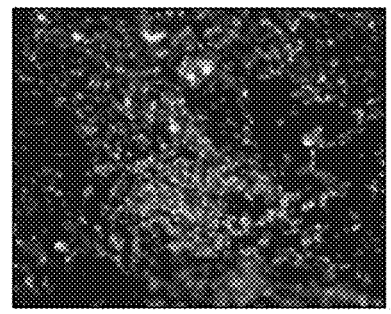
FIG. 5D depicts CD8+ T-cell infiltration of B16 melanoma tumors in cells treated with CDN and GVAX.

FIG. 4 demonstrates the dose-dependency of the therapeutic benefit exhibited by the STING-targeted CDN/GVAX combination. In this experiment, 5×10$^4$ B16 melanoma cells were inoculated in the footpad of C57BL/6 mice. Once tumor is palpable at day 6, GVAX (B16 GM-CSF (GVAX), 1.5×10$^6$ cells) or the CDN/GVAX combination at 2, 20, or 200 ng CDN/animal was injected subcutaneously into the contralateral thigh. In the case of the combination treatment, the CDN was formulated with digitonin at 10 µg/mL for 30 min at 20° C. and subsequently washed 4× with PBS to remove non-incorporated CDN prior to injection as described above. Tumor volume was measured daily in a total of 20 animals/treatment group. As shown in the figure, the antitumor response was increased as the concentration of CDN increased from 2 ng/animal to 20 ng/animal, but no further increase was observed by increasing the dosage to 200 ng/mL.

FIG. 5 provides further evidence of a synergistic antitumor response to the CDN/GVAX combination. In this figure, B16 melanoma cells were harvested from the animals and the cells fixed onto slides for immunohistochemistry. Fluorescein-labeled anti-CD8 antibodies were ised to visualize CR8+ T-cell infiltration into the tumor. DAPI was used to counterstain the nucleus of the tumor cells. The four panels shown in the figure are untreated B16 melanoma cells (A), and cells treated with CDN (B), GVAX (C) and CDN/GVAX (D). As shown, a substantial improvement in CD*+ T-cell tumor infiltration is observed with CDN/GVAX in comparison to either of CDN or GVAX alone.

Figure 6:
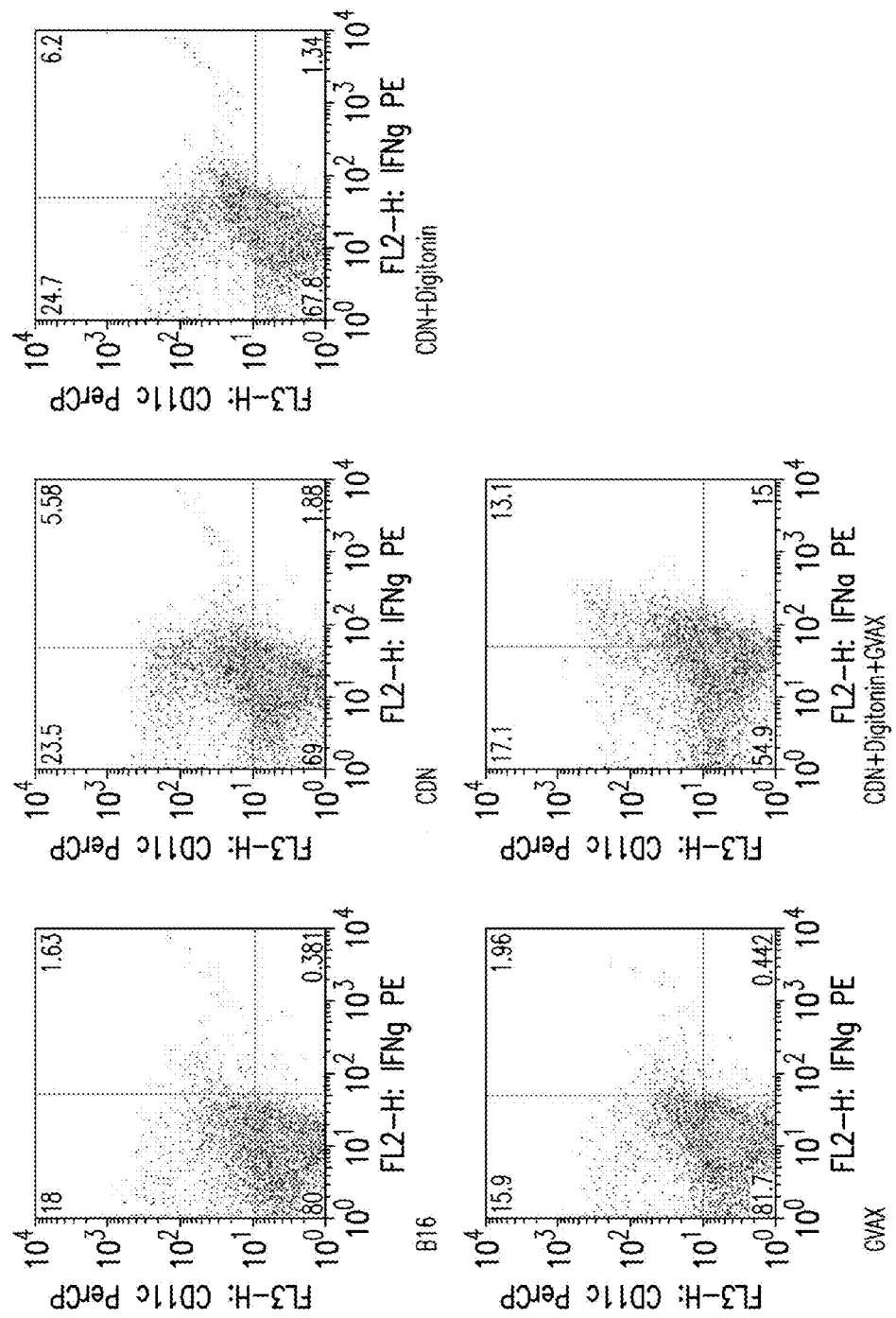
FIG. 6 depicts induction of mature interferon γ-producing splenic DC (CD11c+ cells) in response to a GVAX/CDN combination vaccine.

Similarly, FIG. 6 demonstrates an improved induction of mature interferon γ-producing splenic DC (CD11c+ cells) by CDN/GVAX in comparison to either of CDN or GVAX alone. In this experiment, mice were treated as described above, and the spleen from 2 mice/group were harvested. Total splenocytes were harvested and stained with anti-CD11c and anti-IFNa conjugates. The treatment (untreated B16, CDN, CDN+digitonin, GVAX, and CDN/GVAX+digitonin) are indicated in the figure.

Example 3

Figure 9:
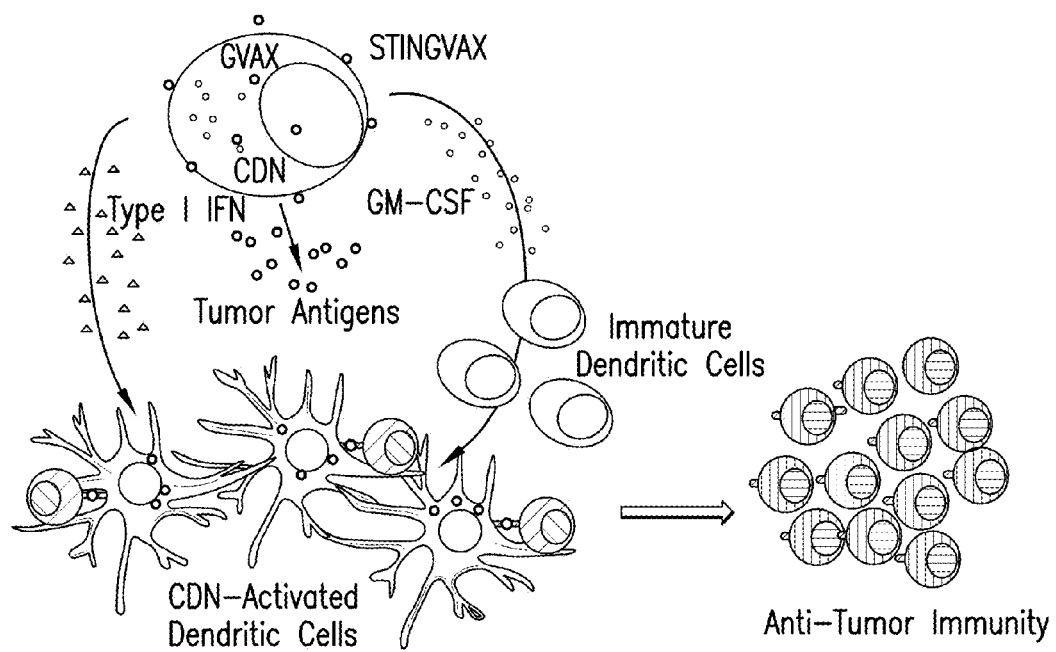
FIG. 9 depicts the synergistic mechanism of action of "STINGVAX."

FIG. 9 depicts the synergistic mechanism of action of "STINGVAX," which is STING-activating cyclic purine dinucleotides co-formulated with irradiated GM-CSF expressing allogeneic tumor cells (GVAX; STING+ GVAX=STINGVAX). The GVAX tumor cell vaccines provides an un-biased presentation of multiple tumor associated antigens to the immune system. GM-CSF produced by GVAX recruits dendritic cells (DCs) to the injection site. CDNs activate the recruited DCs, which in turn activate or prime potent antigen-specific CD4 and CD8 T cells that traffic to and kill the tumor, resulting in a clinical benefit. STINGVAX can enhance the tumor response either by serving as a depot for the GM-CSF recruited DCs, or through autocrine signaling express both TBK-1/IRF-3 dependent IFN-β and NF-κB pro-inflammatory cytokines that in combination activate the GM-CSF recruited DCs.

The mechanism for the increased anti-tumor efficacy of STINGVAX is believed due to the activation of innate immunity that is mediated by direct binding of CDNs to STING, triggering a conformational change in this receptor, resulting in signaling through the TBK-1/IRF-3 axis and activation of type 1 interferons (IFN), including IFN-α and IFN-β. GM-CSF produced by the GVAX tumor cell vaccine recruits dendritic cells (DCs) to the injection site. CDNs activate the recruited DCs, which in turn activate or prime potent antigen-specific CD4 and CD8 T cells that traffic to and kill the tumor, resulting in a clinical benefit.

Figure 8:
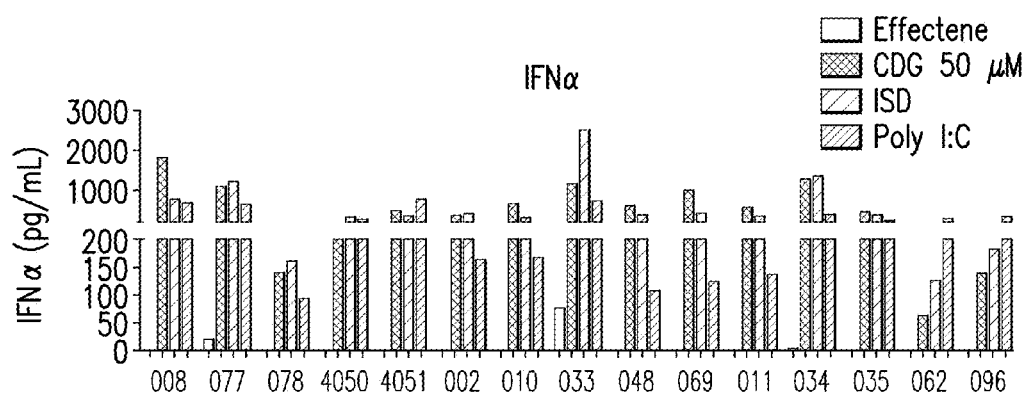
FIG. 8 depicts the expression of IFN-α in cultured human peripheral blood mononuclear cells isolated from 15 independent donors, following stimulation with various activators of innate immunity, including cyclic-di-GMP (CDG), Interferon Stimulating DNA (ISD), and poly inosine-cytosine (Poly I:C).

To determine the levels of IFN-α as a signature of CDN potency to activate innate immunity, 1×10$^6$ primary human PBMCs isolated from fifteen independent human donors were incubated in a 96 well U bottom plate for 30 min at 37° C., 5% CO2 with 50 µM of c-di-GMP (CDG), 1 µg/mL of Interferon Stimulatory DNA (ISD), or 4 µg/mL of Poly (I:C) utilizing Effectene transfection reagent (Qiagen) to transfer the molecules into the PBMC. ISD (Interferon Stimulating DNA) is TLR independent (Stetston, D. B. et. al. Immunity 24, 93-103, January 2006) and signals through cGAS, and is thus STING-dependent, while Poly (I:C) can signal through both TLR3 and RIG-I pathways, and are thus STING-independent. After 30 minutes, the cells were washed and replaced with RPMI media containing 10% FBS and incubated at 37° C., 5% CO2. After 24 hours incubation IFN-α levels were determined by Cytometric Bead Array (CBA, BD Biosciences) (FIG. 8). These results demonstrate that cyclic-di-GMP activates innate immunity in human leukocytes prepared from multiple independent donors, thus supporting the mechanism of action of STINGVAX.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

The invention claimed is:

1. A composition comprising:
   a cyclic purine dinucleotide which binds to STING and induces STING-dependent TBK1 activation; and
   an inactivated tumor cell which expresses and secretes granulocyte-macrophage colony-stimulating factor (GM-CSF).

2. A composition according to claim 1, further comprising a pharmaceutically acceptable excipient.

3. A composition according to claim 1, wherein the tumor cell is inactivated by treatment with radiation.

4. A composition according to claim 1, wherein the cyclic purine dinuclotide is selected from the group consisting of c-di-AMP, c-di-GMP, c-di-IMP, c-AMP-GMP, c-AMP-IMP, and c-GMP-IMP, or combinations thereof.

5. A composition according to claim 1, wherein the cyclic purine dinuclotide is formulated with one or more lipids.

6. A composition according to claim 5, wherein the cyclic purine dinuclotide is formulated with digitonin.

7. A composition according to claim 5, wherein the one or more lipids form a liposome.

8. A composition according to claim 1, further comprising one or more adjuvants.

9. A composition according to claim 8, wherein the one or more adjuvants comprise CpG and/or monophosphoryl lipid A.

* * * * *

UNITED STATES PATENT AND TRADEMARK OFFICE
CERTIFICATE OF CORRECTION

Page 1 of 1

PATENT NO. : 9,770,467 B2
APPLICATION NO. : 13/912960
DATED : September 26, 2017
INVENTOR(S) : Thomas W. Dubensky, Jr. et al.

It is certified that error appears in the above-identified patent and that said Letters Patent is hereby corrected as shown below:

Column 1
At Line 9, delete:
"BACKGROUND OF THE INVENTION"

And replace it with:
-- ACKNOWLEDGMENT OF GOVERNMENT SUPPORT
This invention was made with government support under DE018464, awarded by the National Institutes of Health. The government has certain rights in the invention.

BACKGROUND OF THE INVENTION --

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*